United States Patent

Zacoi

[11] Patent Number: 5,190,032
[45] Date of Patent: Mar. 2, 1993

[54] APPARATUS FOR CONTROLLING THE TEMPERATURE OF AN AREA OF THE BODY

[75] Inventor: Thomas N. Zacoi, Pittsburgh, Pa.

[73] Assignee: Federal Leasing Rehab Company, Pittsburgh, Pa.

[21] Appl. No.: 830,438

[22] Filed: Feb. 3, 1992

Related U.S. Application Data

[63] Continuation-in-part of Ser. No. 443,931, Mar. 15, 1990, abandoned.

[51] Int. Cl.$^5$ .............................................. A61F 7/00
[52] U.S. Cl. .................................... 128/400; 128/402
[58] Field of Search ............... 128/400, 402, 399, 379, 128/380, 24 R; 165/46; 219/211

[56] References Cited

U.S. PATENT DOCUMENTS

| | | | |
|---|---|---|---|
| 1,860,847 | 5/1932 | Armstrong | 128/380 |
| 2,566,865 | 9/1951 | Wingerter | 165/46 |
| 3,463,161 | 8/1969 | Andrassy | 128/402 |
| 3,674,034 | 7/1972 | Hardy | 128/379 |
| 3,815,610 | 6/1974 | Winther | 128/380 |
| 3,822,705 | 7/1974 | Pilotte | 128/379 |
| 3,867,939 | 2/1975 | Moore et al. | 128/400 |
| 3,871,376 | 3/1975 | Kozak | 128/403 |
| 3,882,873 | 5/1975 | Arango | 128/379 |
| 3,905,367 | 9/1975 | Dapcich . | |
| 3,995,621 | 12/1976 | Fletcher et al. . | |
| 4,026,299 | 5/1977 | Sauder | 128/400 |

(List continued on next page.)

FOREIGN PATENT DOCUMENTS

| | | | |
|---|---|---|---|
| 0475811 | 11/1937 | United Kingdom | 128/402 |
| 2202447 | 6/1988 | United Kingdom | 128/400 |

OTHER PUBLICATIONS

"dependable THERM-O-RITE" Advertisement-1965.
Hot/Ice Dual Function system—Revised Jul. 1987 (4 pages).
InCare Hot/Ice System Knee Blanket Holder—copyrighted 1989 (1 page).
Thermal Power On The Spot—copyrighted 1989 (1 page).
Cold Therapy Made Easy—DURA*KOLD compression Ice Wrap System copyrighted 1989 by DePuy (4 pages).
DURA*KOLD Re-usable Compression Ice Wraps Advertisement (2 pages).
Post-Op Cryotherapy and DURA*KOLD-Nov. 1989 (4 pages).
DURA*KOLD Hand-outs (3 pages).
DURA*KOLD Professional Prices Jan. 1990 (1 page).
Corporate Profile (article)—DURA*KOLD (1 page).
REDI-GRIP hip spica Support (2 pages).
Tecnol—Orthopedic Soft Goods (6 pages).
STERLING'S therapeutic gel wrap—handout (2 pages).
ELASTO GEL—Therapy Products (4 pages).
DERMA—COOL Treatment Packs (2 pages).

*Primary Examiner*—Mark Graham
*Attorney, Agent, or Firm*—James L. Sherman

[57] ABSTRACT

An apparatus is for use with a temperature controlled fluid circulating device which apparatus controls the temperature of an area of the body. The apparatus includes a fluid circulating blanket having connecting hoses for connection to the fluid circulating device. The fluid circulating blanket is installed within the interior of a support envelope surrounding the fluid circulating blanket. The fluid circulating blanket and surrounding support envelope respectively include parallel elongated portions with connecting portions therebetween to provide an overall U-shape with an elongated opening between the parallel elongated portions of each of the blanket and support envelope. The apparatus includes straps for securely positioning the support envelope, with the fluid circulating blanket therein, with the inside surface of the support envelope against the area of the body. The inside surface of the support envelope includes cloth material while the outside surface of the support envelope includes insulation material.

18 Claims, 8 Drawing Sheets

U.S. PATENT DOCUMENTS

| | | | |
|---|---|---|---|
| 4,033,354 | 7/1977 | De Rosa | 128/379 |
| 4,042,803 | 8/1977 | Bickford | 219/211 |
| 4,081,150 | 3/1978 | Tyson | 128/402 |
| 4,107,509 | 8/1978 | Scher et al. | 219/211 |
| 4,114,620 | 9/1978 | Moore et al. | |
| 4,149,541 | 4/1979 | Gammons et al. | 128/400 |
| 4,202,325 | 5/1980 | Villari et al. | 128/24 R |
| 4,335,726 | 6/1982 | Kolstedt | 128/400 |
| 4,338,944 | 7/1982 | Arkans | 128/400 |
| 4,372,318 | 2/1983 | Viesturs et al. | 128/403 |
| 4,459,468 | 7/1984 | Bailey | |
| 4,470,417 | 9/1984 | Gruber | 128/402 |
| 4,523,594 | 6/1985 | Kuznetz | 128/402 |
| 4,527,566 | 7/1985 | Abare | 128/402 |
| 4,556,055 | 12/1985 | Bonner | 128/821 |
| 4,585,003 | 4/1986 | Meistrell | 128/402 |
| 4,586,506 | 5/1986 | Nangle | 128/403 |
| 4,614,189 | 9/1986 | Mackenzie | 128/380 |
| 4,688,572 | 8/1987 | Hubbard et al. | 128/402 |
| 4,736,088 | 4/1988 | Bart | 219/211 |
| 4,742,827 | 5/1988 | Lipton | 128/380 |
| 4,753,240 | 6/1988 | Sparks | 128/379 |
| 4,753,241 | 6/1988 | Brannigan et al. | 128/380 |
| 4,846,176 | 7/1989 | Golda | 128/400 |
| 4,951,665 | 8/1990 | Schneider | 128/400 |
| 5,016,624 | 5/1991 | Kanare | 128/402 |

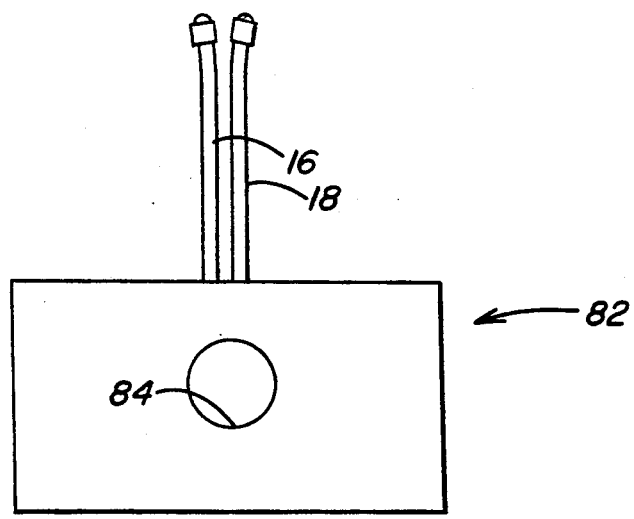
FIG. 10 PRIOR ART
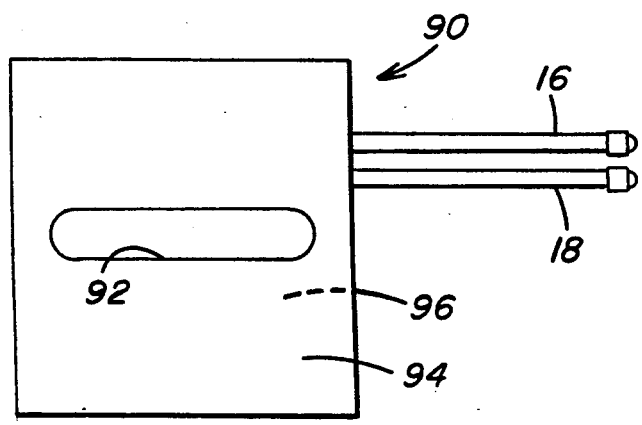
FIG. 11
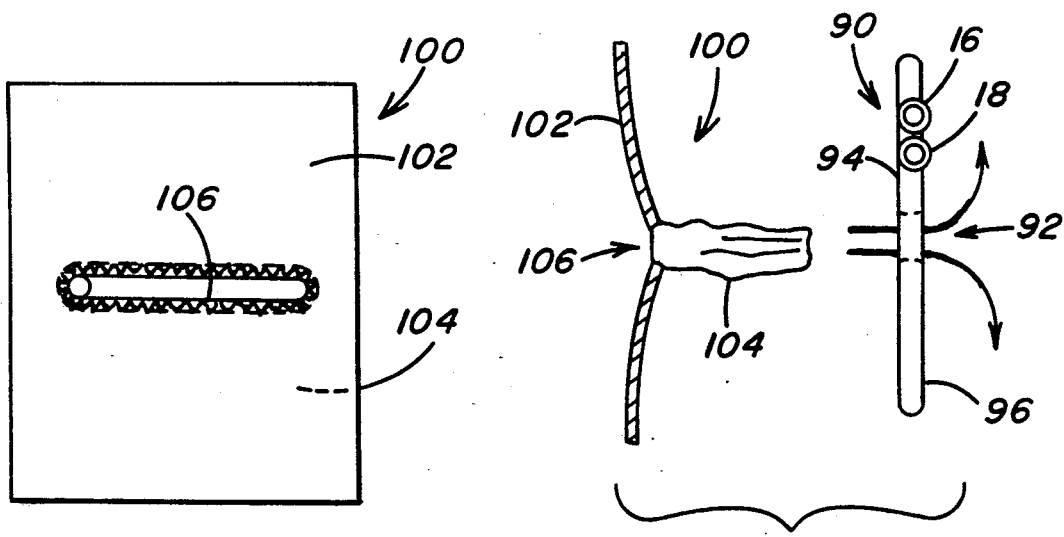
FIG. 12
FIG. 13

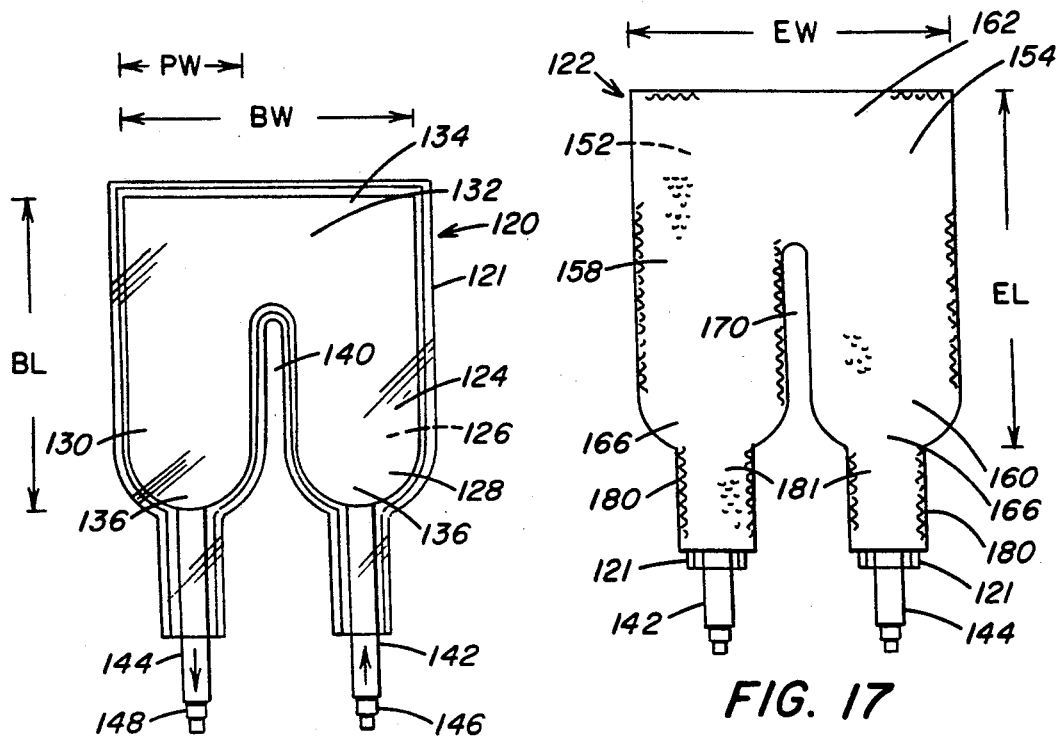
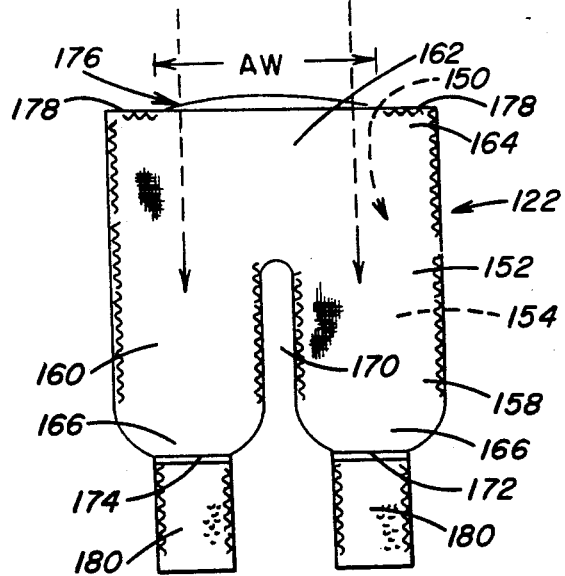
FIG. 16
FIG. 17
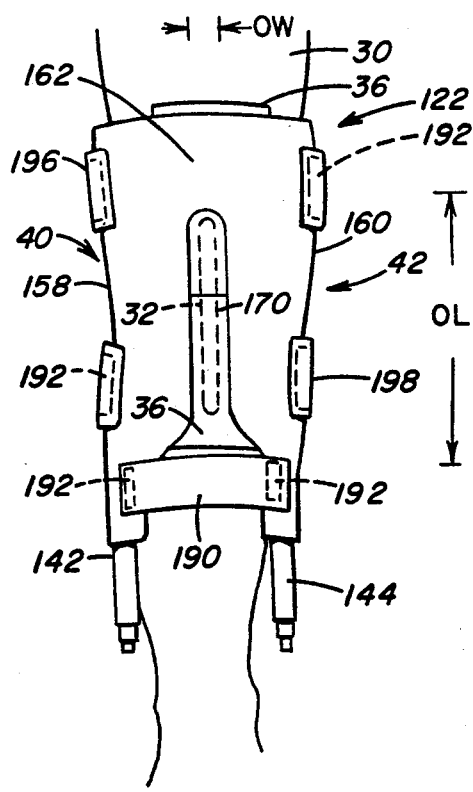
FIG. 18

APPARATUS FOR CONTROLLING THE TEMPERATURE OF AN AREA OF THE BODY

This application is a continuation-in-part of U.S. patent application Ser. No. 07/443,431 filed on Mar. 15, 1990, abandoned.

BACKGROUND OF THE INVENTION

1. Field of the Invention

This invention relates to an apparatus for controlling the temperature of an area of the body for therapy or for improved recovery following surgery.

2. Description of the Prior Art

It has been found that to improve patient healing and recovery by reducing pain, swelling, and blood loss, post-operative procedures increasingly employ means for reducing the temperature in the area of the body around the surgery.

For example, after a knee operation, an ice pack or other device for reducing the temperature is applied to the area around the surgery. The area of incision, after closure, may be initially covered with a light sterile gauze. At one time, after knee surgery, the leg and knee would simply be covered with additional sterile gauze, additional sterile padding and finally wrapped from the toe to the groin with an elastic, ace bandage until the first dressing change. The ace bandage caused a compression on the leg that tended to reduce swelling and decreased the likelihood of phlebitis. Early attempts to reduce the temperature following knee surgery included applying ice packs or the like to the surface of the ace bandage in the knee area. However, the padding and bandage insulated the surgical area and made the cooling ineffective for properly reducing pain, swelling and/or blood loss.

If there were to be a means for more efficiently directing cold to the area of surgery, it would preferably be capable of extended and controlled generation of a reduced temperature. Although such a device for controlling temperature need not lie immediately against the area of incision, proper post-operative procedures require that all of the components employed in the surgical area be properly sterilized.

It would seem possible that any prior art means for holding a heat source or a cold source, such as ice, might be employed to significantly improve the likelihood that the source could be maintained in a proper position on the patient. However, a number of such devices which are primarily used for therapeutic procedures have not been found to be appropriate for post-operative procedures. Some such therapeutic devices include electrical heating pads or bandages such as those disclosed in U.S. Pat. Nos. 4,042,803; 4,107,509; and 4,736,088. Some heating pad configurations employ pouch devices in which warm water or chemical substances, which combine to form heat, are installed for the therapeutic application of heat to the patient. Such devices have been disclosed in U.S. Pat. Nos. 3,815,610; 4,470,417; and 4,742,827.

Because the preferred post-operative procedure would include means for cooling the area of the surgery, various devices, which are primarily intended to cool an area of a body, would appear to be more significant. However, some cooling devices are for use on animals rather than people. They tend to employ ice which is subject to melting or a means for directing cool liquid to the area but do not appear to have any direct application in a post-operative environment. Such devices are disclosed in U.S. Pat. Nos. 1,860,847; 3,905,367; 3,822,705; 4,033,354; and 4,556,055. U.S. Pat. No. 1,860,847 discloses a ring-shaped flexable bag for hot or cold water for the treatment of cold, influenza or similar ailments.

A more extensive number of devices have been suggested for the therapeutic application of heat or cold to the human body. Such devices typically include some form of support device or wrapping device having pouches or pockets for the insertion of a hot pack or a cold pack. The cold pack may contain ice or some chemically reactive material for producing a lower temperature. Since these devices employ hot water and/or cold water or ice, the amount of time that such a device can be employed is clearly limited. The loss of heat or cold may be acceptable for therapeutic uses but is clearly undesirable for post-operative procedures. Such devices for use on various parts of the body are disclosed in U.S. Pat. Nos. 3,882,873; 4,081,150; 4,372,318; 4,586,506; 4,527,566; 4,614,189; 4,688,572; 4,753,240; and 4,753,241.

Because of the limited heating or cooling duration of the various devices discussed hereinabove, there was clearly a need for some system which is capable of applying a continuously adjustable and monitored source of heat or cold to a desired area of the body. U.S. Pat. Nos. 4,459,468 and 4,844,072 are directed to temperature controlled, fluid circulating systems which, perhaps, best represent the type of systems which are enjoying increased acceptance in the therapeutic as well as the surgical field. These particular fluid circulating systems are designed for use with a thermal blanket or pad and includes temperature controis so that both heating and cooling effects could be selectively produced through the preheating or precooling of the fluid. The fluid is pumped through the thermal blanket to provide proper heating or cooling as desired at the location of the thermal blanket. For this purpose, the thermal blanket includes supply and discharge hose means which can be conveniently coupled to and uncoupled from the overall system. For proper operation of the overall system, various sizes and shapes of thermal blankets are provided for heating or cooling different areas on the patient.

Similar fluid circulating systems are disclosed in U.S. Pat. Nos. 3,674,034; 3,995,621; 4,026,299; 4,202,325; 4,335,726; 4,338,944; and 4,523,594.

U.S. Pat. No. 3,674,034 is directed to a system for maintaining controlled deep body temperature by providing heat to efficient areas of a person's body. The system includes a series of pouches which are individually strapped to the neck, each arm pit, and each upper thigh at the groin area of a person. Each pouch consists of a cloth covered tubing array and is connected to a hypothermia machine for controlling the temperature of the body in areas where the blood arteries are close to the skin surface. Since each pouch includes a thin, low-porosity and highly thermal-conductive fabric covering the tubing array therein, efficient heat transfer is produced without burning the patient. Each of the covers is said to be removable for laundering and sterilization. However, there is no suggestion that the device could or even should be utilized in a surgically sterile area for treatment of a patient.

The device disclosed in U.S. Pat. No. 3,995,621 includes a liquid cooled brassiere and is directed to a method of diagnosing malignant tumors. The device is not appropriate for nor applicable in post-operative procedures.

U.S. Pat. No. 4,202,325 is directed to a compression device having an improved fastening sleeve. The device is for applying compressive pressure against the patient's limb from a source of pressurized fluid and, again, has no post-operative application for directing heat or cold to a surgical area.

U.S. Pat. Nos. 4,335,726 and 4,338,944 disclose a therapeutic device with temperature and pressure controls. The therapeutic device includes a sleeve for covering a portion of a patient's body and has a space to receive cool circulating liquid. The device also incorporates means for applying pressure to the area of the patient to be cooled. As a result, it is recommended that this therapeutic device be used, for example, by sports trainers for the application of cold and pressure to the extremities, hands, feet, or joints of an athlete after a sprain or strain sustained during playing. Similarly, it is said that physicians in hospitals, such as emergency rooms, may employ such a device to apply cold and pressure to a patient in order accelerate healing by reducing edema and hematoma. If either such procedure were to periodically require heat, the overall therapeutic device could be readjusted for the periodic application of heat. There is no suggestion of the device being capable of being employed post-operatively.

U.S. Pat. No. 4,026,299 discloses a portable heating and cooling apparatus which utilizes flexible pads to be wrapped around a limb or other body portion of a human or animal. The portable apparatus is said to be especially useful for treating sprains, strains or other muscular injuries to athletes or race horses as soon after the injury occurs as possible in order to rapidly reduce swelling, fever or the like to the injured area. The overall system primarily employs flexible pads with a complicated array of flexible tubing loops which could be covered by a removable, non-insulating sheet which is intended to be applied to and lie against the patient's limb. This inner sheet could become soiled or worn and thus could be removed, washed or otherwise cleaned for sanitary purposes, or replaced. However, there is nothing to suggest that the apparatus would be appropriate for modern post-operative procedures which are performed in a surgically sterile environment.

U.S. Pat. No. 4,523,594 discloses a stretchable textile heat-exchange jacket. This heat-exchange jacket can be wrapped about and conform to a limb, an arm or a body member and function therapeutically to heat or cool the member. The jacket is formed of a sheet of elastic fabric material having an array of flexible plastic pipes threaded therethrough. The respective ends of the flexible pipes were coupled to an inlet fluid distributor and an outlet fluid collector. The elastic sheet is provided at its opposing sides with complimentary fabric fastener components to releasably hold the jacket securely in place on the body member even when the member is being flexed. Although this stretchable textile heat-exchanger jacket is clearly intended for therapeutic use during limited movement of a limb or joint, the general background of the invention discusses a possible use of cold following knee, leg or other surgery on an extremity where there is usually swelling in the vicinity of the incision.

U.S. Pat. No. 4,523,594 indicates that when the wound is dressed in a surgical bandage, it becomes difficult to apply ice to the site to reduce swelling and promote healing. Moreover, since surgical bandages, casts and rubberized braces used during rehabilitation are relatively impermeable to perspiration and act as thermal barriers, there is often a build-up of moisture and heat during a surgical dressing. This could create a climate conducive to bacteria. Such bacterial activity could cause infection and retard the healing process. The textile-heat exchange jacket is considered to be thin enough to be fitted under an "existing" surgical cast, bandage or brace without discomfort, whereby the jacket, when cold, could serve to reduce swelling and arrest perspiration in the wound area and also act to relieve post-operative itching.

The stretchable textile heat-exchanger jacket includes a rectangular sheet of fabric woven or otherwise fabricated of elastic cotton fibers, spandex or other natural or synthetic stretchable fabric material capable of being sterilized by conventional hospital procedures. However, threaded into the fabric sheet is a parallel array of flexible pipes formed of synthetic plastic material. While the pipes are stitched into the fabric sheet, most of the tubes surfaces are exposed and engage the body member when the jacket is wrapped thereabout. Alternatively, the sheet could take the form of two superimposed plies of open-mesh, stretchable fabric, with the pipes sandwiched therebetween in a manner in which the pipes form ducts between the plies.

Despite the discussions in U.S. Pat. No. 4,523,594 regarding possible use in surgical ares, the device disclosed therein is not particularly adapted for nor appropriate for post-operative procedures. The particular heat-exchange system is clearly intended to function therapeutically to heat or cool the member and even includes a suggestion of connecting the loop system to a water faucet of a house sink which then supplies tap water to the jacket. With the confusing arrangement of tubes connected to the stretchable jacket material, the entire system has been found to be too complicated to be practically employed in an operating room and poorly configured for post-operative use.

Despite the plurality of devices discussed hereinabove, an extensive number of surgeons do not employ any means for the post-operative reduction of temperature in the surgical area. This continues to occur despite the fact, as discussed hereinabove, that temperature reduction can be more conveniently and reliably directed to a surgical area with various types of thermal blankets or pads employed in a system such as those disclosed in U.S. Pat. Nos. 4,459,468 and 4,844,072. The blankets are provided extended, double hoses and couplings for convenient, quick and reliable connection to the overall system. Some fluid circulating blankets or pads, such as those disclosed in U.S. Pat. Nos. 4,114,620 and 4,149,541 are primarily intended for therapeutic use but are representative of the increased interest in flexible blankets for use with such temperature controlled, fluid circulating systems. Because the temperature of the blankets can be controlled for an extended period of time with the fluid circulating system, the blankets have been used in post-operative procedures as well as the initially intended therapeutic procedures. With limited but increasing acceptance of the blankets in post-operative procedures, it is not uncommon for the thermal blankets to be pre-sterilized for use in an operating room. Such sterilized blankets are disclosed in U.S. Pat. Nos. 3,867,939 and 4,951,665.

Although the thermal blankets themselves are a reliable and effective source of cold, the post-operative procedures with the blankets presently being employed by surgeons are extremely complicated, time-consuming and unreliable. Typically, for example, after a knee operation, two sterilized blankets are removed from sterile packages by a nurse. The blankets are to be directed to opposite sides of the knee, adjacent the specific area of the incision. An attending nurse is also required to remove at least two pieces of 4 inch by 8 inch sterile gauze which are packed in a peel pack. One or more sterile gauze pieces are then laid on the interior surfaces of the two blankets. The nurse must then orient the double hoses which extend from each blanket towards the foot of the patient. The nurse is usually positioned toward the body side of the knee with the surgeon positioned toward the foot side of the knee. Both blankets with the gauze pieces thereon are dispose, gauze up, for eventual alignment on either side of the knee area. Next, two sterile A.B.D. pads, which are thicker and about 5 inches by 10 inches, are removed from a peel pack for application on the outer side of each of the blankets. With the gauze thereon and with the A.B.D. pads applied to the outside of each blanket, it is not uncommon for the blankets and pads to be misaligned or poorly positioned against the opposite sides of the knee area by the nurse and/or the surgeon.

With the surgeon holding the sterile gauze, blanket, and A.B.D. pad in each hand against opposite sides of the knee, the nurse begins to wrap the knee area from the thigh to below the knee with a sterile gauze roll. It is not uncommon for the surgeon's hands to be partially enwrapped or for the blankets or pads to be further misaligned as the wrapping of the gauze roll proceeds through the knee area. The double hoses extending from the bottom of the blankets must be positioned to extend outwardly of the wrapping as it continues toward the foot. As a result, the hoses of the two blankets may be at different lengths or awkwardly positioned on one side or the other of the leg to complicate eventual connection to the overall fluid circulating system. For patients having shorter legs, the blankets may be oriented with the hoses extending upwardly by the thigh. The same complications of different lengths and awkward positioning can occur.

Finally, an ace bandage is wrapped from the toe to the groin with the ends of the two double hoses again being left exposed and extending outwardly from each of the blankets in order to allow the connection to the fluid circulating system. Even the application of the ace bandage is complicated if the initial positioning and wrapping results in the blanket or the ends of the double hoses being poorly positioned.

After surgery, the blanket is normally maintained adjacent the surgical area in the manner described for as long as three to five days prior to the first dressing change. As will be seen, the first dressing change can also be significantly complicated if the blankets, etc. have not been properly positioned after the surgery. Some surgeons believe the surgical area should be cooled for up to 8 days after the surgery. At that time, the gauze pieces, A.B.D. pads, gauze roll, and ace bandage may all be discarded as the knee continues to be treated therapeutically. Without a proper configuration, the blankets could also be discarded prior to therapy. However, if the configuration would not interfere with flexure of the knee, the blanket could be employed to apply heat or cold during therapy.

Because of the problems discussed hereinabove with positioning and maintaining the blankets in alignment with the area to be cooled, some surgeons apply sterile tape directly to the patient's body around the entire circumferential edge of the thermal blanket. Use of this much tape on the body for an extended period of time can result in a deleterious effect on the skin and, particularly, on the skin of elderly patients. Additionally, despite the normal shaving in the area of the surgery, the area to be shaved may be required to be increased because of the application of tape to the thermal blanket. Finally, eventual removal of the tape is extremely painful to many patients.

A primary objective of the invention is to present an improved apparatus for controlling the temperature of the body which is particularly adapted for use in an area following surgery. However, the primary benefit of such an improved apparatus may be the overall reduction in the time required to position and secure the thermal blankets in the operating room. During surgery, the patient is usually anesthetized. It is well known that a primary concern in surgery includes the patient's reaction to and condition when under anesthesia. Any portion of the surgery or post-operative procedure which can reduce the overall time that the patient is under anesthesia is most significant and highly desirable.

Finally, as mentioned hereinabove, a significant number of surgeons do not even attempt to control the temperature in the area of surgery during the post-operative procedure. Because of the complications encountered with the existing systems, many surgeons do not incorporate any means in the post-operative procedures for reducing the temperature in the area of surgery. This occurs despite the clear indication that reducing the temperature in the area of the surgery can reduce the pain, swelling, blood loss of the patient and significantly reduce the time required for the patient to stay in the hospital. As a result, any means which can increase the acceptance and use of the control of the temperature in the surgical area will enable surgeons and hospitals to ultimately benefit an increasing number of patients.

All of the patents discussed hereinabove are incorporated by reference as if the entire contents thereof were included herein.

OBJECTS OF THE INVENTION

It is an object of the invention to provide an apparatus for controlling the temperature in the area of a body.

It is another object of the invention to provide such an apparatus which will reduce the pain, swelling, blood loss and hospital stay of the patient following surgery.

It is still another object of the invention to provide such an apparatus which can be efficiently, effectively, and reliably employed by a post-operative team.

It is still another object of the invention to provide such an apparatus which will reduce the time that a patient must be anesthetized following surgery.

It is yet another object of the invention to provide such an apparatus which is particularly configured and adapted for use in the knee area of a leg.

It is also an object of the invention to provide such an apparatus which could be used to post-operatively provide cooling at the sides of a mid-line incision of the knee.

It is a further object of the invention to provide an apparatus of the type described which will allow access to and be free of contact with the incision in the knee.

It is also an object of the invention to provide an apparatus of the type described which will allow flexure of the knee area for therapeutic reasons or for improved recovery following surgery.

THE SUMMARY OF THE INVENTION

These and other objects of the invention are provided in a preferred embodiment thereof including an apparatus for use with a temperature controlled fluid circulating device for controlling a temperature of an area of a body. The apparatus includes a fluid circulating blanket having a first side and a second side. The fluid circulating blanket has two parallel elongated portions and a connecting portion therebetween. The parallel elongated portions has first ends and second ends with connecting portion being at the first ends to form an elongated opening between the parallel elongated portions. The fluid circulating blanket has a fluid connection hose extending from an edge of the second end of each of the parallel elongated portions. The fluid connection hoses include extended ends adapted to be connected to the fluid circulating device. A support envelope surrounds the fluid circulating blanket to enclose at least the first side and the second side within an interior of the support envelope. The support envelope includes an inside surface adjacent the first side and an outside surface adjacent the second side. The support envelope has two parallel elongated envelope portions and a connecting envelope portion therebetween. The parallel elongated envelope portions have first ends and second ends with the connecting envelope portion being at the first end to form an elongated envelope opening between the parallel elongated envelope portions. The elongated envelope opening is in alignment with the elongated opening of the fluid circulating blanket. The inside surface and the outside surface are joined at least at an edge of the elongated envelope opening. There are straps for securely positioning the support envelope, with said fluid circulating blanket therein, with the inside surface of the support envelope against the area of the body. The inside surface of the support envelope includes cloth material. The outside surface of the support envelope includes insulation material.

Support envelope includes an access opening at the first ends of the parallel elongated envelope portions and the connecting envelope portion therebetween for insertion of the fluid circulating blanket within the interior of the support envelope. The fluid circulating blanket includes a blanket width along the first end of the parallel elongated portions and the connecting portion, the access opening includes an access width along the first end of the parallel elongated envelope portions and the connecting envelope portion, and the access width is less than the blanket width for retention of the fluid circulating blanket within the interior of the support envelope. Each of the parallel elongated envelope portions of the preferred embodiment includes a hose opening at the second end for extension of the fluid connection hose from the interior of the support envelope to dispose the extended end outwardly of the support envelope. The straps for securely positioning the support envelope includes an adjustable strap extending between the second ends of the parallel elongated envelope portions and the adjustable strap is for establishing an opening width of the elongated envelope opening at the second ends of the parallel elongated envelope portions. The outside surface of the support envelope and the adjustable strap includes releasable connecting surfaces therebetween. The outer surface of each of the parallel elongated envelope portions at the second end thereof includes an extended portion which extends beyond the second end of each of the parallel elongated portions of the fluid circulating blanket. The extended portion of the outer surface of each of the parallel elongated envelope portions includes a support element for fluid connection hose which extends from the edge of the second end of each of the parallel elongated portions. The adjustable strap is secured to the extended portion of the outside surface of each of the parallel elongated envelope portions.

For one preferred embodiment, the area is a surgically sterile area of the body which surgically sterile area surrounds a surgical region of the body following surgery. The fluid circulating blanket and the support envelope are sterile. The straps for securely positioning the support envelope, with the fluid circulating blanket therein, is for aligning the elongated opening and the elongated envelope opening with the surgical region when the inside surface of the support envelope is against the surgically sterile area. When the surgery includes a mid-line incision of a knee, the mid-line incision defines the surgical region, the surgically sterile area of the body is at opposite first and second sides of the knee and the mid-line incision thereof, and the elongated opening and the elongated envelope opening include an opening width of at least ¼ inch and an opening length of at least 8 inches for the alignment with the mid-line incision. The parallel elongated envelope portions respectively overlay the first and second sides of the knee. The straps for securely positioning the support envelope include retaining strap devices which extend around a leg and the retaining strap devices are sterile. The straps for securely positioning the support envelope can also include an adjustable strap extending between the second ends of the parallel elongated envelope portions and the adjustable strap is sterile. The adjustable strap is disposed at least 8 inches from the connecting envelope portion. The adjustable strap is for establishing the opening width of the elongated envelope opening at the second end of the parallel elongated envelope portions.

In the preferred apparatus, the fluid circulating blanket includes a blanket width of about 12 inches and a blanket length of about 12 inches. Each of the parallel elongated portions includes the blanket length of about 12 inches and a portion width of at least 6 inches.

BRIEF DESCRIPTION OF THE DRAWINGS

FIG. 10 is a plan view of another prior art fluid circulating blanket.

FIG. 11 is a simplified view of an improved fluid circulating blanket.

FIG. 12 is a simplified view of a preferred support envelope for installation on the improved fluid circulating blanket of FIG. 11.

FIG. 13 is a side view of the support envelope of FIG. 12 demonstrating the installation of the support envelope on the fluid circulating blanket of FIG. 11.

FIG. 16 is a simplified view of the inward side of an improved fluid circulating blanket as it is being inserted within an interior of a corresponding improved support envelope including various features of the invention.

FIG. 17 is a simplified view of the outward side of the improved support envelope of FIG. 16 with the improved fluid circulating blanket installed within the interior thereof.

FIG. 18 is a schematic view of the knee area following the preparation step of FIG. 2 in which the improved support envelope of FIG. 17 has been installed on the knee in a manner similar to the method employed with two blankets as shown in FIG. 9.

DETAILED DESCRIPTION OF THE PREFERRED EMBODIMENTS

Prior to the detailed description of the preferred method and apparatus for post-operatively controlling the temperature of an area of the body after surgery, it is appropriate to specifically discuss the existing fluid circulating blankets and some of the detailed steps which are presently required for their use in post-operative procedures.

Figure 1:
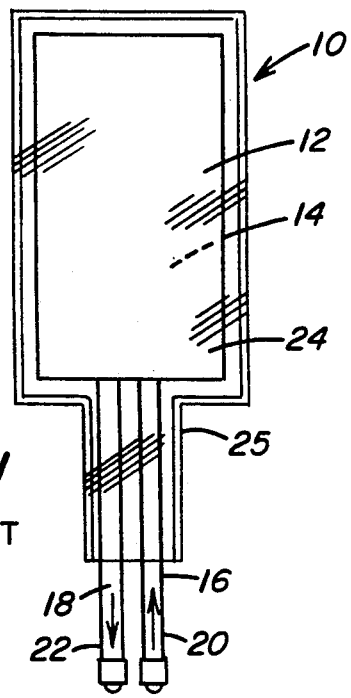
FIG. 1 is a simplified view of a typical prior art fluid circulating blanket.

As seen in FIG. 1, a typical fluid circulating blanket 10 would include a first side 12 and a second side 14 which are formed of sealed plastic material for retaining pressurized fluid therein. Fluid connecting hose means in the form of an inlet hose 16 and an outlet hose 18 are connected to one edge of the blanket 10. When properly connected to a temperature controlled, fluid circulating system of the type described hereinabove, cool fluid will be supplied as indicated by the arrow 20 and the warmer fluid will be a discharge as indicated by the arrow 22. The blanket 10 includes an array of internal passages or channels (not shown) for directing the fluid throughout the blanket in an effort to provide generally even heating or cooling at the first side 12.

The prior art fluid circulating blanket 10 may also include a surrounding, clear plastic container 24 to provide a means for collecting condensation or moisture which would tend to collect on the first side 12 and the second side 14 of the fluid circulating blanket 10 during use. The plastic material of the container 24 is relatively thin and non-insulating to allow the transfer of heat or cold from the blanket to the patient. The plastic container 24, because of the thin plastic material, could only collect a limited amount of unpressurized fluid if there were any minor leaks in the fluid circulating blanket 10 after it is installed on a patient. Some such containers 24 include a hose portion 25 which extends from the major portion of the blanket 10 to also surround the hoses 16, 18.

Fluid circulating blankets 10, as shown in FIG. 1, are typically provided for both therapeutic and surgical uses. However, for surgical applications, the fluid circulating blanket 10 (including the hoses 16 and 18 and the container 24) are sterilized prior to their being used in an operating room.

Acceptable sterilization for post-operative procedures would include gamma radiation, steam heating in a steam autoclave, or, preferably, sterilizing with ETO gas (Etholene Oxide Gas). With most of the components of the preferred fluid circulating blanket 10 being formed of plastic material, steam sterilization would clearly be inappropriate and ETO gas is preferred. Prior to sterilizing, the fluid circulating blanket 10 is placed inside a package (not shown) which is then sealed. The package with the fluid circulating blanket 10 enclosed therein is placed in an ETO gas chamber for sterilization. The ETO gas completely permeates the package and the fluid circulating blanket therein. The preferred sterile package for surgery includes a double-packaging configuration. In other words, the blanket 10 is placed inside a sealed interior package which is then, in turn, placed inside a sealed exterior package. With both the interior and exterior packages being sterilized in the ETO gas, the overall configuration is less likely to be contaminated during the surgery. The exterior package can be opened in a non-sterile area with the sterile interior package being placed inside of the sterile boundary during surgery. The sterile interior package can then be opened for convenient handling of the sterilized fluid circulating blanket within the sterile surgical area.

It will be noted, during the description provided hereinbelow, that reference to the fluid circulating blanket 10 may include the container 24 thereon. Since some fluid circulating blankets 10 do not include such a container 24 and those which do include a container 24 are basically positioned and used in the same manner as the overall fluid circulating blanket 10, reference to the fluid circulating blanket 10 in the explanation of the preferred method of operation will apply whether there is or is not a container 24. It should also be noted that the portion 25 of the container 24 of FIG. 1 extends for some length along the hoses 16, 18. However, not all containers 24 extend as far from the major portion of the blanket 10 itself. Further, the light plastic material of container 24 at the portion 25 does not really support the hoses 16, 18 and can not be relied upon to retain them together even if it does extend for some distance from the major portion of the blanket 10.

Similarly, when referring to various means for sterile packaging for the components to be described hereinbelow, reference to the package could include both an interior package and an exterior package. Again, unless otherwise indicated, the overall operation would not be appreciably changed whether there is a single or double packaging configuration.

Having generally explained a typical fluid circulating blanket 10 and the method of sterilizing and packaging the blanket 10, it is appropriate to describe a typical operation in which such a blanket 10 has been employed. As mentioned hereinabove, the application of cold has been advantageously employed for various types of knee surgery. Whether the surgery is total knee surgery or, for example, surgical arthroscopies including lateral release, the controlled and effective application of cold to the area reduces the pain, swelling, blood loss and the length of hospital stay of the patient.

Figure 2:
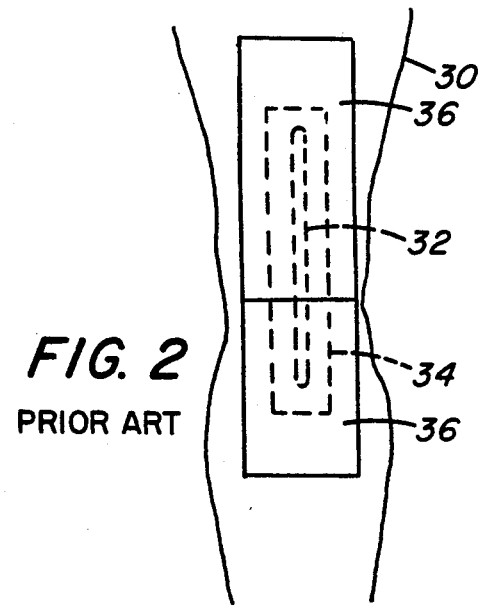
FIG. 2 is a schematic view of the typical prior art method of preparing the right knee of a patient following knee surgery.

As seen in FIG. 2, a typical knee surgery of a right leg 30 would include a mid-line incision 32. The incision 32 is usually closed by surgical staples and results in a gathering of the skin which is about ⅜ inch wide, ¼ inch high, and 8 to 12 inches long. Directly over the closed incision 32, there is placed a petroleum impregnated, sterile gauze material 34 which tends to adhere to the incision area and serves as a sterile barrier for the incision area. The surgeon will typically lay 4 inch by 8 inch gauze pieces 36 on the knee to further protect the incision 32 and the petroleum impregnated gauze 34 thereon.

The leg and knee area would typically be prepared as seen in FIG. 2, even if the surgeon chose not to include any means for reducing the temperature in the surgical area. In such situations, the area would be further dressed with A.B.D. pads, wrapped with an expandable gauze material roll, and then wrapped from the toe to the groin with an ace bandage for providing compression to the entire leg area. However, as mentioned hereinabove, some surgeons and post-operative teams have recognized the advantages of installing the fluid circulating blankets 10 in the knee area for proper cooling during the post-operative procedure. The prior art method, as discussed hereinabove, included an installation in the most simple and basic form on a relatively small leg. With the preferred blanket 10 being about 5 inches by 10 inches and the sterile gauze pieces about 4 inches by 8 inches, a single piece of gauze may simply be laid on the first side 12 of the fluid circulating blanket 10 when applied to the side of a small leg.

Figure 3:
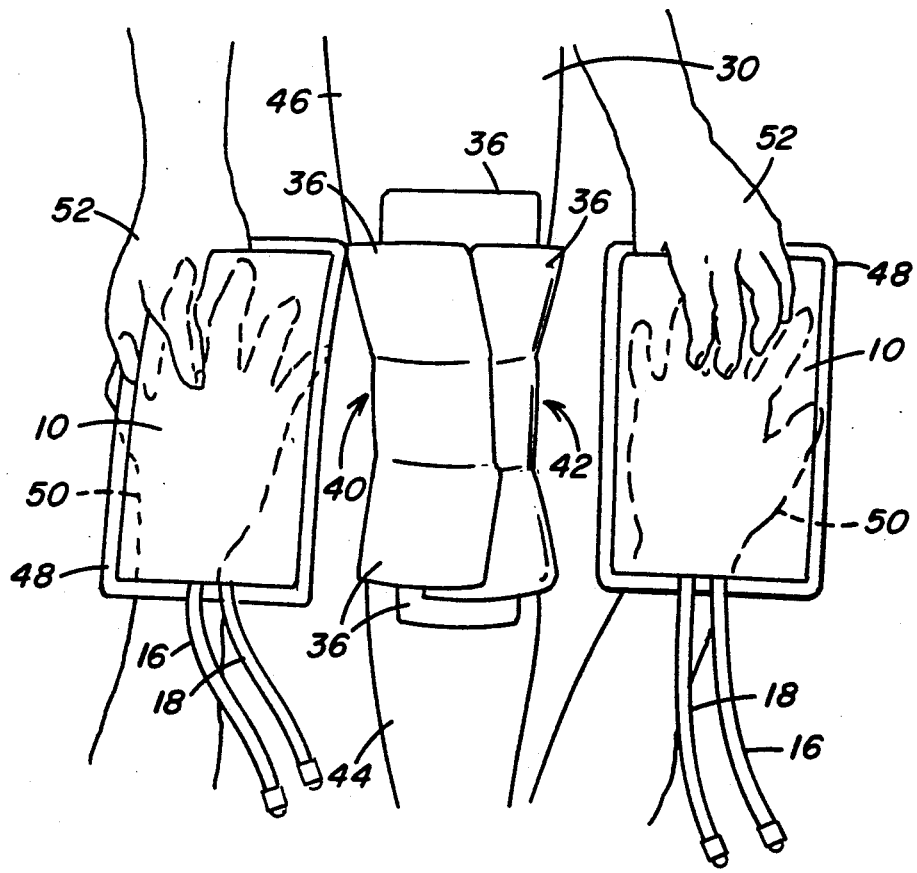
FIG. 3 is a schematic view demonstrating a prior art method of arranging the prior art blankets of FIG. 1 for alignment with the sides of the knee following knee surgery.

However, as seen in FIG. 3, with a larger leg 30, three 4 inch by 8 inch sterile gauze pieces 36 are laid in an overlapping manner on the lateral side 40 while three 4 inch by 8 inch sterile gauze pieces 36 are also laid in an overlapping manner on the medial side 42 of the knee area. Of course, the 4 inch by 8 inch gauze pieces must be individually removed from sterile peel packs. With the six overlying pieces 36 in position, an attending nurse removes two of the fluid circulating devices 10 from their respective sterile packages and two relatively larger A.B.D. pads from their respective sterile packages. As mentioned above, the A.B.D. pads are relatively thick and tend to provide insulation and cushioning on the outside of the fluid circulating blankets 10. The A.B.D. pads generally allow for swelling and expansion in the knee area and provide insulation to form a thermal barrier to direct the cold to the knee area. With the surgeon located at the toe end 44 of the leg 30 and an attending nurse at the upper end 46 of the leg, an A.B.D. pad 48 may be placed on the palm of each hand 50 of the surgeon. The fluid circulating blanket 10 is then placed by the nurse 52 on the top of each of the A.B.D. pads 48 with each set of hoses 16, 18 extending toward the toe end 44 of the leg 30.

Figure 4:
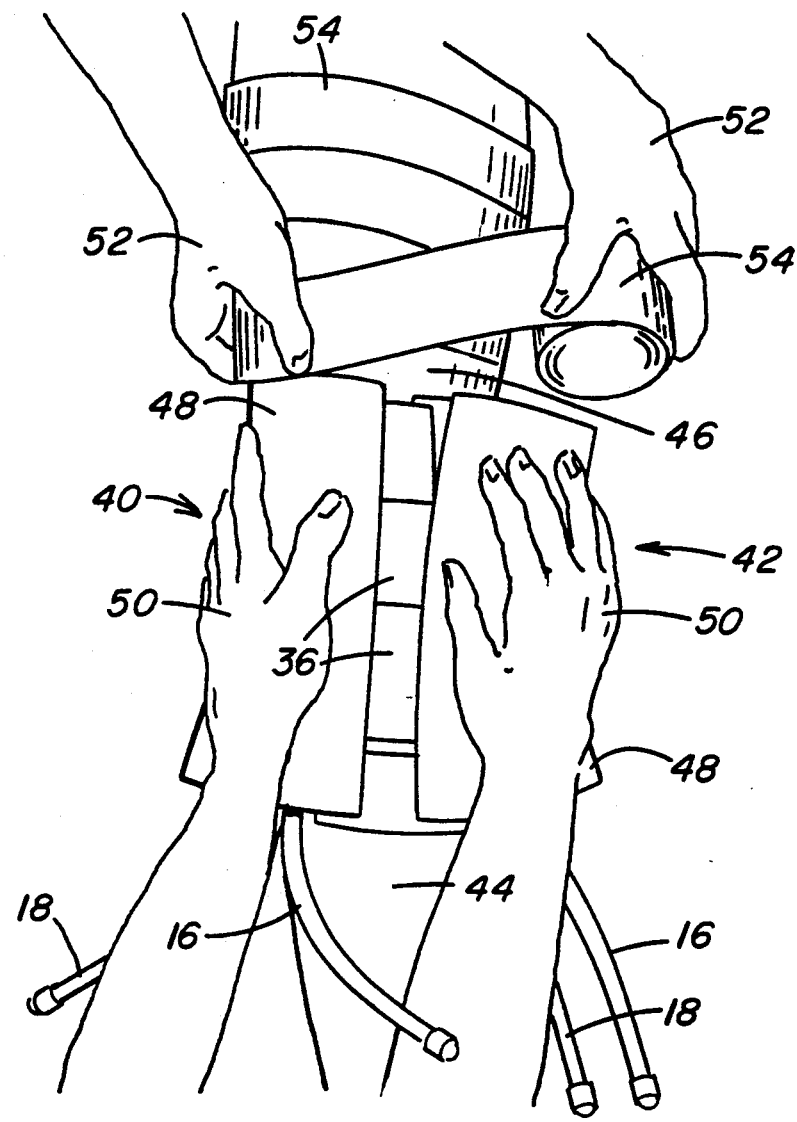
FIG. 4 is a schematic view of the prior art method of positioning the prior art blankets against the sides of the knee following knee surgery.

As seen in FIG. 4, the surgeon will, by hand, direct the fluid circulating blankets 01 and the A.B.D. pads 48 against the lateral and medial sides of the knee area. With the blankets 10 and pads 48 properly positioned, the attending nurse will begin wrapping the leg 30 from the upper end 46 to the lower end 44 with a roll of stretchable, sterile gauze material 54. Wrapping in this manner to retain the pads 48 and blankets 10 against the sides of the knee area is very difficult because of the tendency to wrap and entrap the surgeons hands 50 inside of the wrapped gauze material 54. The schematic views shown in FIGS. 3 and 4 include a preferred alignment which is not easy to obtain during actual postoperative procedures. Although the blankets 01 tend to be flexible, they clearly resist bending around the curve of the leg 30 at both ends 44 and 46. The surgeon and nurse are required to work in a limited area and tend to get in each other's way. In fact, although not shown in FIGS. 3 and 4, additional operating attendants are frequently needed to raise and hold the leg 30 in order to facilitate the wrapping of the gauze material 54 around the leg. Additionally, it is also unclear from the schematic views just how cumbersome and awkward the extended hoses 16 and 18 tend to be while trying to maintain the fluid circulating blankets 10 in proper alignment at opposite sides of the incision area.

Figure 5:
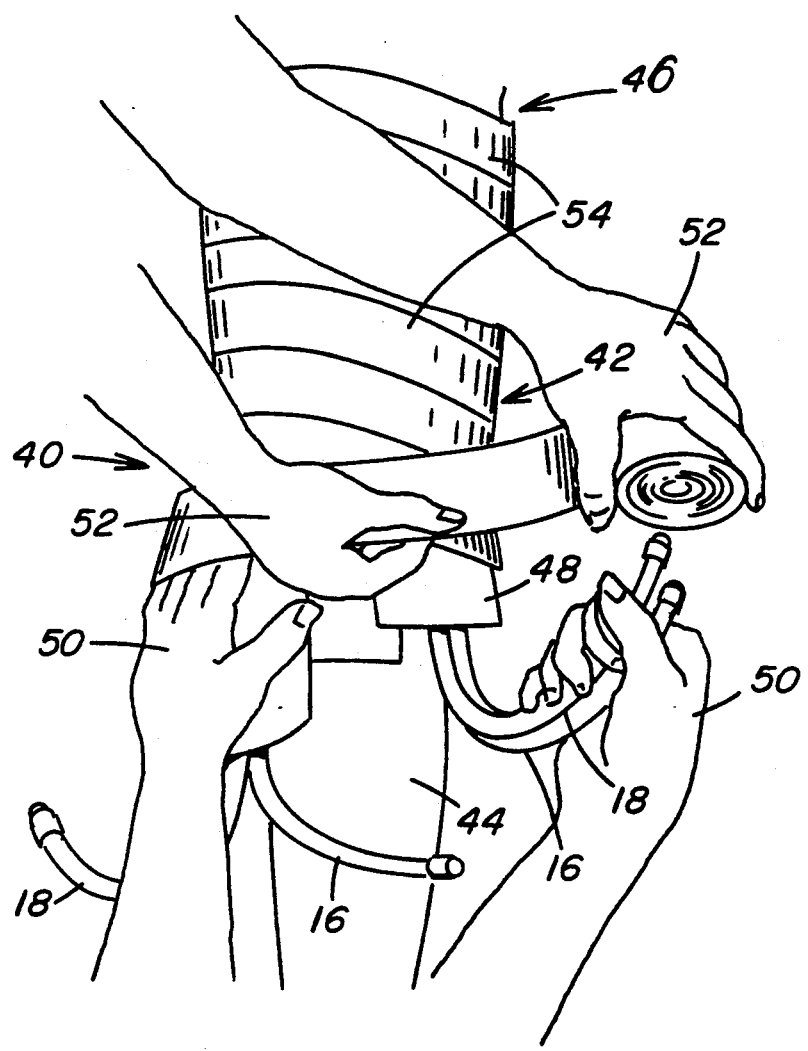
FIG. 5 is a schematic view demonstrating the difficulty of maintaining the prior art blankets in position by the prior art method of positioning.

Continued wrapping of the roll of gauze material 54 also requires attention to and alignment of the connection hoses 16 and 18 of each fluid circulating blanket 10. For example, as seen in FIG. 5, the wrapping to include the fluid circulating blanket 10 at the medial side 42 of the knee has been relatively effective so that the surgeon is no longer required to hold the blanket 10 at the medial side 42. However, unfortunately, by way of example, the blanket 10 at the lateral side 40 has been allowed to slip down toward the lower end 44 of the leg. Since the nurse is attempting to wrap the surgical area with the gauze material 54 in a manner which does not include the connection hoses 16, 18, one hand 50 of the surgeon will direct the connection hoses 16, 18 of the blanket 10 at the medial side 42 outwardly for continued wrapping while still trying to use the other hand 50 for properly maintaining the blanket 10 at the lateral side 40. Obviously, with continued wrapping and assuming that the hand 50 at the lateral side may be withdrawn, the connection hoses 16 and 18 of the blanket 10 at the lateral side 40 must also be held in an outward position as the wrapping toward the toe by the nurse continues. It should be noted that if the nurse were to drop the roll of gauze material 54 onto the operating floor during the wrapping, the wrapping would be removed and redone with a fresh sterile roll of material 54.

Of course, even with continued wrapping, as generally demonstrated in FIG. 5, the respective hoses 16, 18 of each of the blankets 10 may extend from the leg area in different positions and may be forwardly or rearwardly disposed on the leg to generally complicate a connection to the fluid circulating machine. Generally, it should be clear that the procedure described hereinabove is extremely complicated, cumbersome, awkward, and unreliable. The actual positions of the fluid circulating blankets 10 is not assured and the bending or dislocation of the connection hoses 16, 18 is very likely.

At first glance; different locations for the extended ends of the hoses 16, 18 would not seem to present any significant problems. However, some fluid circulating systems employ a single fluid discharge hose and a single fluid return hose. When two blankets are employed, a relatively small yoke fitting is attached to the end of each of the discharge and return hoses. Both inlet hoses 16 must be connected to the yoke fitting of the discharge hose and both outlet hoses 18 must be connected to the yoke fitting of the return hose. If the hoses 16 and the hoses 18 are poorly positioned, they may be bent or crimped as they are directed to the common yokes. The reduction or loss of normal flow could cause the entire system to be automatically turned off.

The complicated and cumbersome prior art method described hereinabove is repeatedly performed by skilled surgeons and attending nurses. However, some surgeons tend to allow physician's assistants and/or hospital technicians to attempt to install the blankets. Any problems experienced by surgeons would be increased if less skilled personnel are involved and the likelihood of successful and rapid placement would be significantly reduced.

In either case, after the complete wrapping of the gauze material 54, the leg, with the connection hoses 16, 18 again extending therefrom, is wrapped from the toe end 44 all the way to the groin end 46 with an ace bandage (not shown). The ace bandage maintains the gauze material 54, the A.B.D. pads 48, the fluid circulating blankets 10 and the gauze pieces 36 in position, even if misaligned, and under compression until a time for changing the first dressing.

The post-operative control of temperature, with the fluid circulating blankets 10 connected to the temperature controlled, fluid circulating system described hereinabove, would typically continue for 3 to 5 days. After the 3 to 5 days, the post-operative team will inspect the surgical area and apply a fresh dressing. The ace bandage is removed and the wrapped gauze material 54 and gauze pieces 36 are gently cut apart in the mid-line area of the incision. The soiled petroleum impregnated gauze 34 is then removed for direct inspection of the incision 32. For this to be properly done, the blankets 10 must be slightly pulled outwardly from the area of the incision, as the wrapped gauze material 54 is gently pulled back, in order to inspect the entire incision 32. Assuming there is no infection or undesired fluid build up in incision 32, a new strip of petroleum based gauze 34 is again applied to the incision 32. With additional gauze pieces 36 laid over the top thereof, the cut gauze material 54, the blankets 10 and pads 48 are simply realigned to be adjacent the incision area as a new ace bandage is again wrapped about the entire leg. The ace bandage will again properly retain the gauze material 54, the pads 48, the blankets 10 and the gauze pieces 36 and 34 and produce compression on the leg as the blankets 10 are connected to the fluid circulating system for continued control of the temperature in the area of the knee surgery. From this discussion of the examination of the surgical area at the time of the first dressing change, it should be clear that the proper alignment of the pads 48 and blankets 10 are again critical in order to be able to ensure access to the incision 32.

The present invention is directed to improving the method and apparatus discussed hereinabove to more conveniently and reliably locate various fluid circulating blankets adjacent a surgical area. As will be seen, the preferred apparatus utilizes a support envelope for supporting and retaining the fluid circulating blankets therein. Proper use of the support envelopes facilitates positioning and alignment of the fluid circulating blankets 10 and insures that they are efficiently and effectively directed to the desired area to be cooled. Again, by way of example, it is appropriate to discuss how the preferred method and apparatus can be used to improve the recovery of a patient from knee surgery.

Generally, in the description hereinbelow, reference to the right or left side will be the right or left side as viewed in the figures rather than as applied to a patient.

Figure 6:
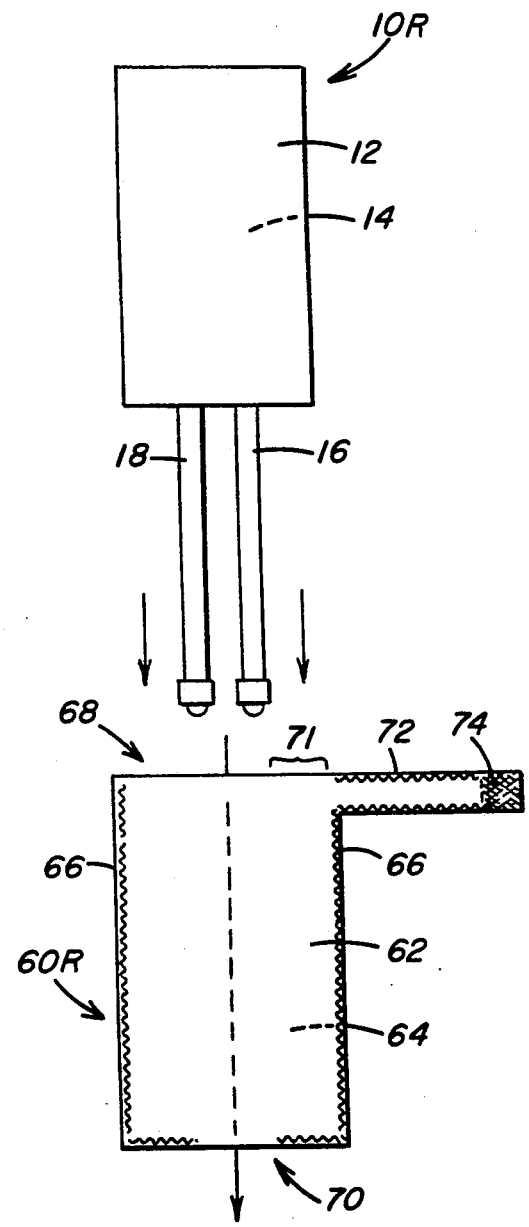
FIG. 6 is a view of the inward side of a preferred support envelope for receiving a fluid circulating blanket for alignment with the right side of the knee.

As seen in FIG. 6, a right fluid circulating blanket 10R, which is identical to the blanket 10, is shown with the first side 12, which is to be directed to the area to be cooled, exposed. The hoses 16, 18 are oriented in a downward position. A preferred right support envelope 60R is positioned with the inside surface material 62 shown for alignment with the first side 12 of the blanket 10R.

Figure 7:
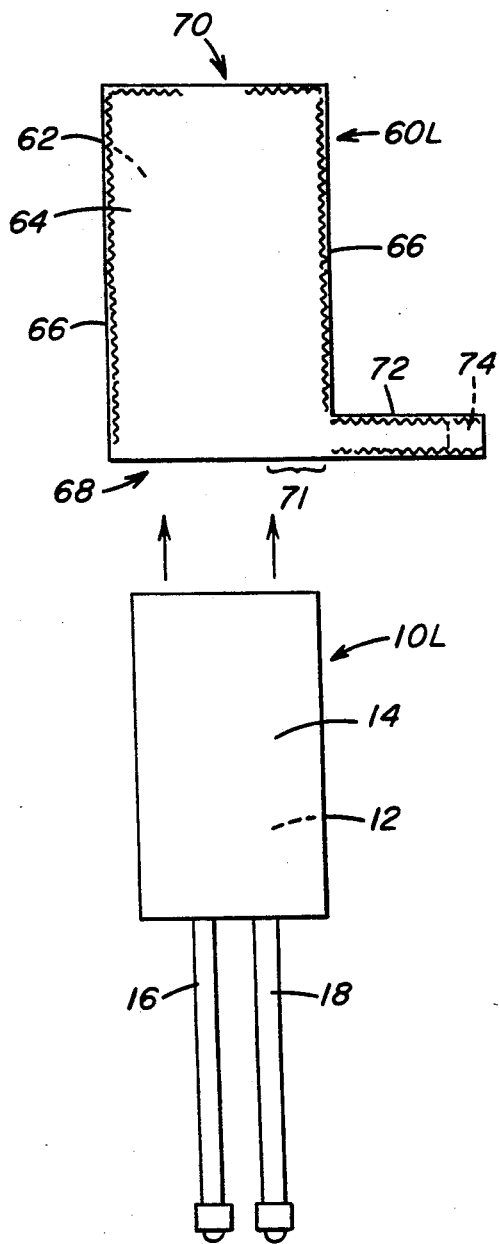
FIG. 7 is a view of the outward side of a preferred support envelope for receiving a fluid circulating blanket for alignment with the left side of the knee.

As seen in FIG. 7, a left fluid circulating blanket 10L, which is identical to the blanket 10R, is disposed with the second side 14 exposed and, again, with the hoses 16, 18 extending downwardly therefrom. A preferred left support envelope 60L is identical to the right support envelope 60R but is shown in FIG. 7 with the outside 64 exposed for alignment with the second side 14 of the left fluid circulating blanket 10L.

With each of the fluid circulating blankets 10R, 10L having dimensions of about 5 inches by 10 inches, the support envelopes 60R, 60L have outside dimensions (approximately 5.5 inches by 10.5 inches) which are slightly larger than but correspond to the outer dimensions of the fluid circulating blankets 10R, 10L for receipt of each of the blankets respectively therein.

Each support envelope 60R, 60L may include the inside surface 62 made of a batiste or similar material which can be directly placed on the skin of the patient but is sufficiently thin and non-insulating to allow effective heat removal by the blanket 10R, 10L. The inside surface 62 may preferrably be formed of a polyester waffle material which is non-irritating, allows the skin to breath, but tends to prevent the growth of bacteria.

The outside surface 64 of each support envelope 60R, 60L may be formed of a polypropylene or other foam material with a loop material laminated thereon. The polypropylene or other foam material can provide insulation to retain the cold in the area of the blanket 10R, 10L for more effective reduction of the temperature in the surgical area. However, the preferred outside surface 64 would be made of a polypropylene felt material which is totally inert, hypo-allergenic and tends to prevent the growth of bacteria therein. Although the polypropylene felt material provides better insulation than the foam material, neither is intended to allow air to move freely therethrough. The outer surface is preferrably provided brushed-pile nylon or polyester on the outside thereof for connection with various hook tab or strip means in a manner described hereinbelow.

As seen in FIGS. 6 and 7, the inside surface 62 and the outside surface 64 of each support envelope 60R, 60L are joined together at edge stitching 66 which only extends partially around the peripheral edge of the support envelope 60R, 60L. R. F. sealing or some other heat sealing means for joining the edges could be used if appropriate for the particular material of the inside surface 62 and outside surface 64. In either case, a large opening 68 at one end and a small opening 70 at the other end allow access to the interior of the support envelope 60R, 60L. The large opening 68 is adapted to allow insertion of the fluid circulating blanket 10R, 10L into the interior of the support envelope 60R, 60L. When properly positioned within the support envelope 60R, 60L, the blanket 10R, 10L will be oriented so that the first side 12 is aligned with and in contact with the inside surface 62 while the second side 14 is aligned with and in contact with the outside surface 64.

However, as seen in FIGS. 6 and 7, the particular blankets 10R, 10L are oriented differently within their respective support envelopes 60R, 60L. The right blanket 10R is installed with the hoses 16, 18 first. Consequently, the hoses 16, 18 are aligned with and extend through the opening 70 at the lower end of the support envelope 60R when the blanket 10R is fully received therein. On the other hand, the left blanket 10L is installed with the hoses 16, 18 disposed away from the left support envelope 60L so that the hoses 16, 18 will extend from the left support envelope 60L through the larger opening 68 when the blanket 10L is fully installed therein. It has been found that the blankets tend to remain within the support envelopes once fully inserted therein.

However, if desired, additional edge stitching or sealing can be provided at 71 which would require the blanket to be slightly bent for insertion. The edge stitching or sealing at 71 would act on a corner of the blanket, after installed, to further insure that it will remain within the interior of the support envelope. An alternative configuration of support envelopes could include different left and right envelopes with only one opening at the lower edge of each envelope as it is to be placed beside the knee. The width of the single opening might be slightly less than the width of the blanket to insure retention of the blanket after it is inserted therein.

Each of the preferred support envelopes 60R, 60L includes connection strap means in the form of a strap 72. The strap 72 is located at one end of the support envelope 60R, 60L and extends from the side edge of the basic support envelope 60R, 60L. Each of the straps 72 includes an extended end having a hook tab 74. The hook tab 74 at the extended end of the strap 72 is located on the same side as the inside surface 62 of the support envelope 60R, 60L.

Figure 8:
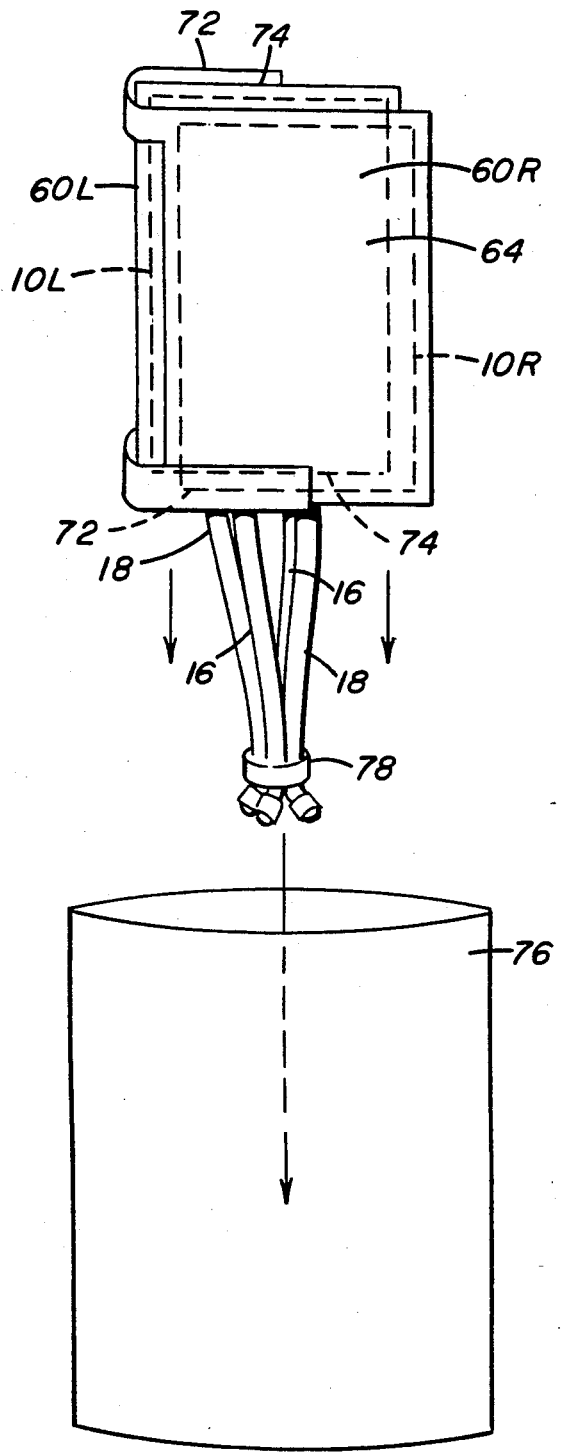
FIG. 8 is a perspective view of the support envelopes of FIGS. 6 and 7 joined together for insertion into a package in preparation for sterilization.

As best seen in FIG. 8, with the blankets 10R, 10L properly installed in the support envelopes 60R, 60L, the envelopes 60R, 60L are connected together by the straps 72 with the respective hoses 16, 18 extending toward the same direction. The hook tabs 74 at the extended ends of the straps 72 are adapted to adhere to the loop surface on the outside 64 of each of the support envelopes 60R, 60L.

To package the combined support envelopes 60R, 60L with the blankets 10R, 10L therein, the envelopes 60R, 60L will be folded together and inserted in a container or package 76. Prior to packaging, the extended ends of both sets of hoses 16, 18 are joined together by rubber band means 78 or the like. As will be seen, this is not intended to simply facilitate installation in the package 76 but will directly contribute to improved positioning and alignment of the support envelopes 60R, 60L, with the blankets 10R, 10L therein, during the post-operative procedure. With the package 76 (whether a single or double configuration) properly sealed with the support envelopes 60R, 60L and the blankets 10R, 10L therein, the entire package and contents are preferably sterilized with ETO gas.

Figure 9:
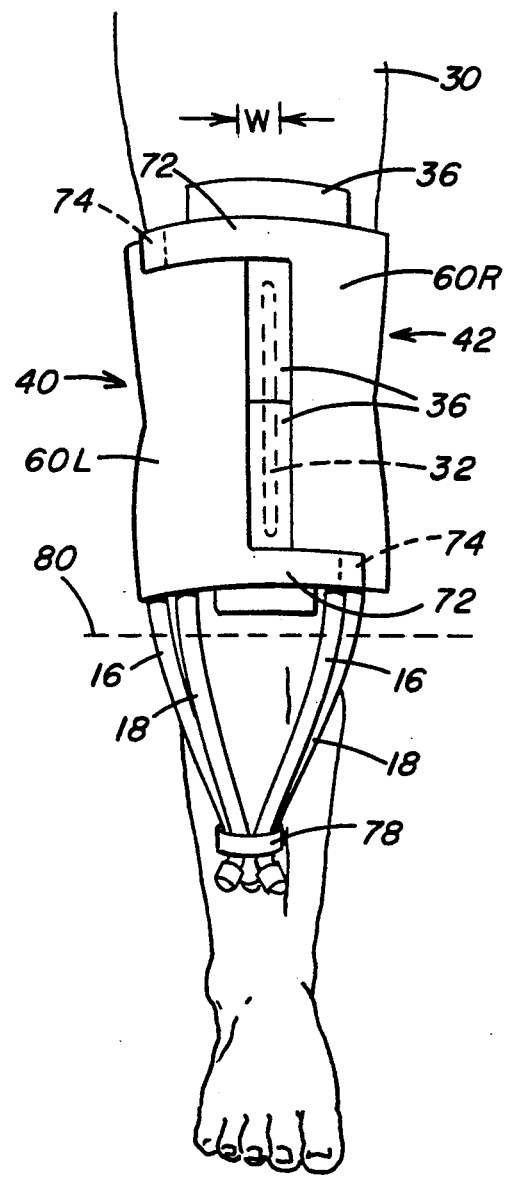
FIG. 9 is a schematic view of the knee area following the preparation step of FIG. 2 in which the preferred support envelopes, having blankets therein, are aligned with the opposite sides of the knee.

As seen in FIG. 9, the surgery to a knee is completed and prepared in the same manner as shown in FIG. 2. The incision 32 has been closed and the gauze 34 and the two gauze pieces 36 positioned directly over the incision 32. With the package 76 opened in the operating room by an attending nurse, the support envelopes 60L, 60R are directly positioned about the incision 32. The hoses 16, 18 from each blanket 10L, 10R extend down the leg 30 of the patient. However, the extended ends of the hoses 16, 18 are retained together by the rubber band means 78.

With the leg 30 in a horizontal position following surgery, the support envelopes 60L, 60R will tend to remain in position by gravity as they support the blankets 10L, 10R herein. With proper positioning of the combined support envelopes 60L, 60R, the strap 72 of the right envelope 60R will be disposed above the area of incision 32 and the strap 72 of the left envelope 60L will be disposed below the incision area 32. Although the support envelopes 60L, 60R are, for packaging purposes, joined together in the general manner as shown in FIGS. 8 and 9, the width W of the aperture between the upper edges of the envelopes 60L, 60R can be selectively adjusted by the surgeon by relocating the hook tabs 74 on each of the straps 72 until the desired width W is obtained.

The preferred method and apparatus eliminates many of the sterilize gauze pieces 36 and the need for applying the A.B.D. pads 48. The functions of these components are more readily, conveniently and reliably provided by the inside material 62 and the outside material 64 of each of the support envelopes 60L, 60R. As a result, positioning the support envelopes 60L, 60R in the manner shown in FIG. 9 prepares the knee area for the wrapping of the leg with the sterile gauze roll material 54.

It should be obvious, from the positioning shown in FIG. 9, that gravity will generally cause the blankets 10L, 10R to be properly positioned respectively at the lateral side 40 and the medial side 42. Actual holding and positioning by the surgeon or the nurse is not really necessary. Interestingly enough, the use of the rubber band means 78 can further assist gravity to insure proper positioning of the blankets 10L, 10R. As the hoses 16, 18, joined at the rubber band means 78, are slightly bent upwardly to lie on the top part of the lower leg of the patient, their natural resilience will tend to cause the blankets 10L, 10R and the support envelopes 60L, 60R thereabout to lie closely against the upper surface of the leg.

The wrapping of the gauze material 54 is significantly simplified with the blankets 10L, 10R retained in the manner as shown. The lower corners or edges may be adjusted by the surgeon or nurse to lie against the lower sides of the leg 30 as wrapping continues down through the incision area 32. However, the attention required by the surgeon or nurse is quite insignificant when compared to the type of support and bending needed for the prior art positioning of the blankets 10 described hereinabove. In fact, the straps 72 positively insure that the upper corners of each blanket 10L, 10R are properly bent and properly positioned about the leg in a manner that was almost impossible to obtain with the prior art procedure.

Although not shown in FIG. 9, wrapping of the support envelopes 60L, 60R through the knee area with the gauze material 54 will continue to a location indicated by the dotted line 80. When the wrapping proceeds to the line 80, both the envelopes 60L, 60R and the blankets 10L, 10R therein are firmly positioned and secured. The hoses 16, 18 can then be bent upwardly from the leg 30 to allow wrapping of the material 54 downwardly toward the foot with each of the hoses 16, 18 exposed for access to the ends thereof. The bending and positioning of the hoses 16, 18 is simplified by the use of the rubber band means 78. Because the blankets 10L, 10R are aligned in equal positions at opposite sides of the knee, the general length of the hoses 16, 18 would be about equal. The common bending at the line 80 allows them to extend from the wrapping with approximately the same length for eventual attachment to the overall fluid circulating system. It should be noted, as seen in FIG. 5, that the prior art method of installing the blankets 10 adjacent the knee area might have required that only one set of hoses 16, 18 be positioned outwardly of the leg while wrapping of the other blanket 10 proceeds with its particular hoses 16, 18 continuing to extend downwardly beside the lower portion of the leg. Later, these hoses 16, 18 must also be bent outwardly for the remainder of the wrapping. The preferred method and apparatus has eliminated separate wrapping and separate bending of the hoses to simplify their positioning and insure that the ends will be accessible. Of course, the convenient positioning of the hoses will also simplify the wrapping of the ace bandage from the toe to the groin in order to apply the desired compression on the leg during the recovery period.

The preferred method and apparatus as shown in FIG. 9 will also facilitate the examination of the incision area 32 at the first dressing change after about 3 to 5 days. With the surgeon having selected the width W, access to the incision 32 is generally assured. The upper edges of the support envelopes 60L, 60R and blankets 10L, 10R are sufficiently pliable to allow tucking and replacement of the gauze pieces 34. In any case, the wrapping with an ace bandage after the first dressing change is clearly simplified by the presence of the straps 72 which maintain the corners of the support envelopes 60L, 60R in general alignment about the leg 30.

The method and apparatus described hereinabove is clearly the preferred. However, as indicated in the discussion of the prior art, the thermal blankets are available from a number of different sources. The preferred method of providing blankets for a knee surgery includes installing the two blankets in the two support envelopes, joining the two envelopes together, inserting them in a common package and then sterilizing the overall package. However, an alternative method for the post-operative application of the blankets might require the actual blankets and support envelopes to be provided in a different manner. For example, with acceptable blankets being separately packaged and sterilized, it would be possible to also provide one or more support envelopes in separate packages for separate sterilization. In the operating room, the blankets could be removed from their packages and the envelopes removed from their package by an attending nurse. An attending nurse would then install the blankets appropriately in their respective envelopes and apply a sterile rubber band means to the ends of the hoses.

The preferred support envelopes 60L, 60R include the integral straps 72. With the possible use of blankets from a separate source or with the possible use of blankets for other areas of the human body, the support envelopes might be alternatively provided with separate strap means which could be positioned at different locations on the support envelopes for retention against the body of a patient. Accordingly, some methods of providing the blankets could include installation of a blanket within an envelope with included, unatttached strap means. The individual blanket and envelope configurations could then be packaged and sterilized for use after a knee surgery. Clearly, various packaging, sterilizing and retaining means with various types of conveniently configured straps could be provided to effectively provide, support and position the blankets in the manner described hereinabove.

It should be recognized that the blankets or the support envelopes might be sterilized by other sterilization means than the preferred ETO gas. Sterilizing in other manners could include sterilization prior to packaging rather than after packaging as preferred with ETO gas.

As clearly demonstrated hereinabove, the preferred use of blankets after a knee surgery includes two such blankets which are about 5 inches by 10 inches. However, as indicated in the prior art discussion, an increasing number of blanket configurations are being provided for special applications. As seen in FIG. 10, one such blanket 82 is about 8 inches by 12 inches and has a circular hole or opening 84 with a 2¼ inch diameter located in the center thereof. The blanket 82 is said to be capable of being utilized following knee surgery or elbow surgery. The opening 84 in the center of the blanket 82 is intended to relieve pressure on and prevent direct contact with the incision in the knee or elbow after surgery. However, as indicated hereinabove, surgery to the knee does not include an incision which is simply located at the knee. The incision may be 8 or more inches long. The entire length is preferably maintained free of any abrasive contact during recovery. The small circular hole 84 in the blanket 82 would result in undesired contact and significantly complicates examination of the incision after the operation. On the other hand, a configuration such as disclosed in U.S. Pat. No. 1,860,843 is not adapted for knee surgery because the large opening would not allow cooling adjacent to the incision area.

As seen in FIG. 11, an improved fluid circulating blanket 90 is configured to provide an alternative to the configuration of FIGS. 6 through 9. The blanket 90 has a length of about 10 inches and a width of about 12 inches to generally provide the same overall dimensions as the two blankets 10R, 10L discussed hereinabove. However, the blanket 90 includes a central elongated opening 92 which is about 8 inches long and about 1.5 inches wide. A single inlet hose 6 and exit hose 18 would be capable of providing cool fluid to both sides of the blanket 90.

Obviously, the blanket 90 could be employed post-operatively in the same general manner as the separate blankets 10 in the prior art manner as shown FIGS. 3 through 5. If used instead of two separate blankets, the blanket 90 would clearly be easier to align with the incision 32 and easier to maintain in position by surgeon. Although, again, gravity would assist in the positioning of both sides of the blanket 90 respectively at the lateral and medial sides of the knee, the surgeon would still be needed to properly position, support and align the additional gauze pieces 36 and the A.B.D. pads 48. Accordingly, an overall preferred configuration would utilize some type of preferred support envelope to eliminate the need for the gauze pieces 36 and A.B.D. pads 48. The general configuration of the support envelopes 60R, 60L would not be appropriate for the blanket 90 because of the need to provide an opening in alignment with the central opening 92 therein.

As seen in FIGS. 12 and 13, one possible support envelope configuration 100 for the blanket 90 would include an outside surface 102 which is again preferably formed of a foam or felt material with a loop material laminated thereon. The inside surface 104 is preferably made of the batiste, polyester or similar material for direct placement against the skin in a non-insulating manner. However, the inside surface 104 and the outside surface 102 are preferably only joined together at the peripheral edge of a centrally positioned opening 106 in the support envelope 100.

Joining of the inside surface 104 and the outside surface 102 in any other location in the preferred support envelope might not result in a smooth abrasive free joining which is preferred. Accordingly, as seen in FIG. 13, in order for the support envelope 100 to be installed on a blanket 90, the inside surface 104 is simply gathered at the region of the opening 106 for insertion through the opening 92 of the envelope 90. With the second side 94 of the blanket 90 properly aligned with and in contact with the interior of the outside surface 102, the gathered inside surface 104 is repositioned and straightened for alignment with the first side 96 of the blanket 90. For most uses, the blanket 90 with the envelope 100 installed thereon could be directed to a surgical area without any need to specifically join the outer edges of the outside surface 102 to the outer edges of the inside surface 104. However, more permanent joining could be provided by stitching or sealing after the blanket is installed or with appropriate hook tabs or hook strips if desired. In either case, positioning on the patient's body could again be provided by separate straps having hook tabs at the ends thereof for connection to and adjustment on the loop outer surface 102. For example, if positioned against the lateral and medial sides of the knee, a simple strap at the top end and a strap at the bottom end could be used to join the respective outer edges of the support envelope 100 as it is folded toward the backside of the leg.

The preferred blanket 90 and support envelope 100 ar equally appropriate for use following an elbow surgery. Again, the alignment of the openings 92, 106 longitudinally along the arm insures that there will be no contact with the incision area when the arm is being bent at the elbow.

It should be noted that during post-operative recovery, it is not uncommon for the leg 30 of the patient to be connected to a motion producing machine. Typically, such a motion producing machine will periodically cause movement of the leg from a 0 degree to a 30 degree bend at the knee during the first day of recovery. The range of motion will typically be increased by about 10 degrees each day until discharge. The objective is to produce a bending motion of 90 degrees at the knee prior to discharge to enable the patient to be able to properly stand from a seated position and to climb stairs during continued recovery in the hospital or at home. However, with a clear objective of mobility in the knee, it is significant that the fluid circulating blankets 10R, 10L and blanket 90 are not directly on the area of incision 32 and are not directed to the popliteal area behind the knee. Locating a fluid circulating blanket in the popliteal area or the incision area 32 might create significant abrasions in either area during the controlled movement of the knee. The resulting abrasions would be extremely undesirable and could be quite damaging.

Abrasion of the incision area is highly likely with the prior art blanket 82. Because of the likelihood of misalignment of the blankets 10 by the prior art method of FIGS. 3 through 5, abrasion of the incision area and/or the popliteal area behind the knee is also likely. In fact, the prior art devices of U.S. Pat. Nos. 4,026,299 and 4,523,594 would clearly damage both the incision area and the popliteal area because of the method taught therein for wrapping around the knee.

Figure 14:
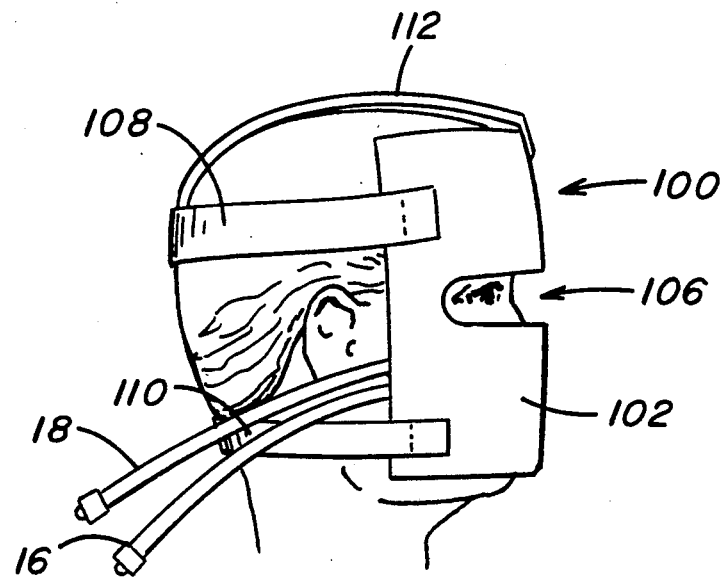
FIG. 14 is a perspective view of one selective positioning of the blanket of FIG. 11 utilizing the support envelope of FIG. 12 on the facial area of a patient.

It has also been found that the preferred blanket 90 and envelope 100 offer additional opportunities for controlling temperature in the facial area following various types of surgery. As seen in FIG. 14, an upper strap 108 including hook tabs, such as that described hereinabove, and a lower strap 110 including hook tabs can be employed to respectively secure the upper and lower areas of the support envelope 100 to cause the first side of the blanket 90 to be retained against the facial area. An additional strap 112 can be extended across the top of the head of the patient to further insure that the blanket 90 and envelope 100 will be retained at the desired position on the face. Although not shown, it will be apparent to those skilled in the art that additional gauze material or ace bandages could be applied to further maintain the blanket 90 and support envelope 100 in position throughout post-operative recovery. In any case, the straps 108, 110, and 112 would generally retain the blanket 90 and support envelope 100 in proper alignment.

Figure 15:
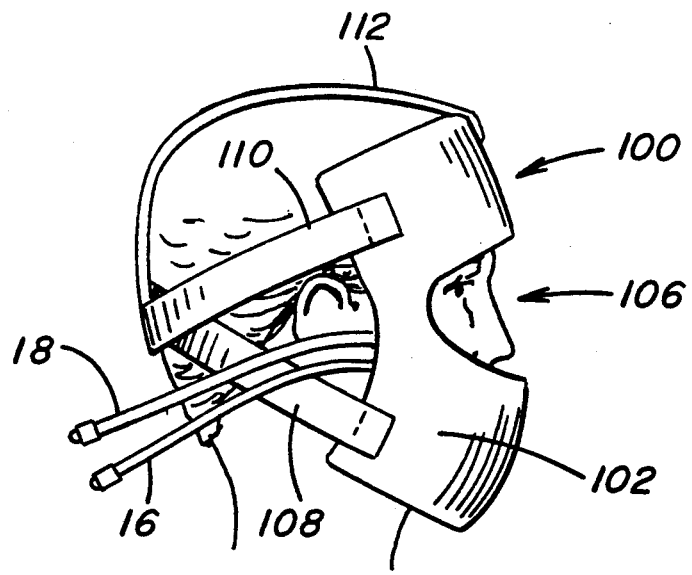
FIG. 15 is a perspective view of another selective positioning of the blanket of FIG. 11 utilizing the support envelope of FIG. 12 on the facial area of a patient.

Although the configuration and alignment shown in FIG. 14 clearly allows the patient to see, the general spacing around the nose also allows the patient to breathe. However, as seen in FIG. 15, should the surgeon determine that the entire nose should be free of contact with the blanket 90, the same preferred blanket 90 can be configured to increase the widths of the openings 92, 106 around the eyes and nose. As seen, a crossing of the straps 108 and 110 produces a curved contour to the blanket 90 and support envelope 100 to relieve both the eye and nose area of the patient. A similar strap 112 can be positioned across the top of the head of the patient to again prevent undesired downward movement of the blanket 90 and insure that the width of the openings are maintained as desired.

It should be noted that the configuration of U.S. Pat. No. 1,860,847 would not be appropriate for use following surgery in the facial area. The bag is elongated in shape so as to extend from the forehead of the patient down to the neck and has a portion adapted to be applied to the forehead of the patient, a portion adapted to extend down along the sides of the face and a portion at the bottom adapted to extend across the front of the neck. The bag is flat in cross section and is provided with an elongated opening in the middle part which clears the eyes, nose, mouth and chin of the patient. Alignment with the nose, cheek or mouth area, as occurs with the configuration shown in FIGS. 14 and 15, would not be possible.

While the embodiments shown in FIGS. 11 through 15 will properly support the fluid circulating blanket disclosed therein, as seen in FIGS. 16 through 18, an improved fluid circulating blanket 120 and an improved support envelope 122 can provide the same functions as the fluid circulating blanket 90 and support envelope 100 therefor.

Specifically, the improved fluid circulating blanket 120 includes a first side 124 and a second side 126. The fluid circulating blanket 120 includes two parallel elongated portions 128 and 130 with a connecting portion 132 therebetween to provide an overall U-shape. The parallel elongated portions 128, 130 have first ends 134 and second ends 136. The connecting portion 132 is at the first ends 134 to form an elongated opening 140 between the parallel elongated portions 128, 130.

The preferred fluid connection hose means is in the form of fluid connection hoses 142 and 144 which are respectively installed at the second ends 136 of each of the elongated portions 128, 130. The fluid connection hoses 142, 144 have extended ends 146, 148 which are adapted to be connected to the fluid circulating device of the type described hereinabove for the circulation of fluid therethrough.

As also seen in FIG. 16, the improved support envelope 122 is adapted to surround the fluid circulating blanket 120. The support envelope 122 is intended to enclose at least the first side 124 and the second side 126 of the blanket 120 within an interior 150 of the support envelope 122. More specifically, the support envelope 122 has an inside surface 152 adjacent to the first side 124 and an outside surface 154 adjacent to the second side 126. The support envelope 122 includes two parallel elongated envelope portions 158 and 160 and a connecting envelope portion 162. The parallel elongated portions have first ends 164 and second ends 166. The connecting envelope portion 162 is at the first ends 164 in order to form an elongated envelope opening 170 between the parallel elongated envelope portions 158, 160.

With the elongated portions 128, 130 respectively installed within the elongated envelope portions 158, 160 and the connecting portion 132 installed within the connection envelope portion 162, the elongated envelope opening 170 will be aligned with the elongated opening 140 of the fluid circulating blanket 120.

In order to install the blanket 120 within the interior 150 of the support envelope 122, an access opening 176 is provided at the first ends 164 of the parallel elongated envelope portions 158, 160 and the connecting envelope portion 162. Each of the hoses 142, 144 must be respectively extended through hose openings 172, 174 at the second ends 166 of the elongated envelope portions 158, 160. Additionally, while the hoses 142, 144 could freely extend from the openings 172, 174, the preferred support envelope 122 also includes hose support means 180.

While the blanket width BW of the fluid circulating blanket 120 is generally defined along the first end 134 of the parallel elongated portions 128, 130 and the connecting portion 132 therebetween, the access opening 176 has an access width AW along the first end 164 of the parallel elongated envelope portions 158, 160 and the connecting envelope portion 162 therebetween. The access width AW is preferably less than the blanket width BW for retention of the fluid circulating blanket 120 within the interior 150 of the support envelope 122. Specifically, the envelope width EW of the support envelope 122 exceeds the blanket width BW but the support envelope 122 is provided edge stitching 178 in order to reduce the access width AW of the access opening 176 for the desired retention within the interior 150 of the support envelope 122. The flexibility of the blanket 120 allows easy insertion within the support envelope 122 but generally prevents its removal after being fully installed therein.

The preferred support envelope 122, as mentioned above, includes the inside surface 152 and the outside surface 154. The preferred joining of the inside surface 152 and the outside surface 154 is at all edges thereof with the exception of the access opening 176 and the hose openings 172, 174. Most significantly, there is included a joining at least at the edges adjacent the elongated envelope opening 170 in order to insure that the edges of fluid circulating blanket 120 surrounding the elongated opening 140 does not come into contact with a portion of the body.

As with the embodiments described hereinabove, the inside surface 152 of the support envelope 122 includes cloth material of the type described hereinabove for being brought into contact with the body. Similarly, the outside surface 154 of the support envelope 122 includes insulation material of the type described hereinabove. As best seen in FIG. 18, the preferred support envelope and fluid circulating blanket configuration includes means for securely positioning the support envelope 122, with the fluid circulating blanket 120 therein, with the inside surface 152 of the support envelope 122 against the desired area of the body.

Clearly, in the preferred configuration, the insulation material forming the outside surface 154 is more rigid and secure than the cloth material forming the inside surface 152. Accordingly, the hose support means 180 for each of the hoses 142, 144 is formed by an extension of the insulation material forming the outside surface 154 which encircles each of the hoses 142, 144 as they extend through the hose openings 172, 174. The general encirclement of the insulation material around each of the hoses 142, 144 supports the hoses as they extend from the second ends 136 of the elongated portions 128, 130 to prevent any bending or crimping which could interfere with the flow of fluid therethrough.

It should be noted that the fluid circulating blanket 120 can include a clear plastic container 121, similar to that shown in FIG. 1, to provide a means for collecting condensation or moisture which would tend to collect on the first side 124 and the second side 126 of the fluid circulating blanket 120 during use. The plastic material of the container 121 is relatively thin and non-insulating to allow the transfer of heat or cold from the blanket to the patient.

As seen in FIG. 17, the improved support envelope 122 includes the fluid circulating blanket 120 therein with the respective hoses 142, 144 extending through the openings 172, 174 (not shown) while being supported by the hose support means 180. Specifically, the outer surface 154 of each of the parallel elongated envelope portions 158, 160 at the second ends 166 thereof includes an extended portion 181 beyond the second ends 166 of each of the parallel elongated portions 158, 160. The extended portions 181 of the outer surface 154 are employed to form the hose support means 180 as they extend from the second end 166 in general alignment with the hose openings 172, 174 (not shown).

In order to generally establish and maintain the opening width OW of the openings 140, 170 as the support envelope 122 and enclosed blanket 120 are installed on a body, the preferred support envelope 122 includes an adjustable strap 190 which generally extends between the second ends 166 of the parallel elongated envelope portions 158, 160. The adjustable strap 190 is for establishing the opening width OW of the elongated envelope opening 170 at least at the second ends 166 of the parallel elongated envelope portions 158, 160.

As seen in FIG. 18, the adjustable strap 190 is preferably formed of an expandable material and includes hook tabs 192 at the ends thereof which rae adapted to adhere to the loop surface of the insulating material of the extended portion 181 of the outside surface 154. While the strap 190 could be located at any position along the outside surface 154, the preferred configuration of employing the extended portion 181 enables the strap 190 to be installed in the region of the hose support means 180 in order to provide the envelope opening 170 with an opening length OL to provide access to a large incision area.

Accordingly, as seen in FIG. 18, the surgery to a knee is completed and prepared in the same manner as shown in FIG. 2. The incision 32 has been closed and the gauze 34 into gauze pieces 36 position directly over the incision 32. The preferred support envelope 122, with the blanket 120 installed therein, can again be packaged with the adjustable strap 190 and additional securing straps 196, 198 within the interior of a package (not shown), similar to that shown in FIG. 8, for sterilization. Such a sterilized package can be opened in the operating room by an attending nurse so that the support envelope 122 could be directly positioned about the incision 32. The hoses 142, 144 extending from the blanket 120 could extend downwardly, as shown in FIG. 18, or, for a patient having a smaller leg, could extend upwardly along the thigh.

With the leg 30 in a horizontal position, the support envelope 122 would tend to remain in position by gravity as it supports the blanket 120 therein. With proper positioning of the support envelope 122, the connecting portion 162 and the strap 190 will be disposed above and below the area of incision 32. Although the strap 190 may be installed prior to packaging, the opening width OW of the opening 170 can be selectively adjusted by the surgeon by relocating the hook tabs 192 on each of the extended portions 181 in order to establish the general desired amount of opening width OW.

Again, the preferred method and apparatus eliminates many of the sterile gauze pieces 36 and the need for applying the A.B.D. pads 48. The function of these components are more readily, conveniently and reliably provided by the cloth material of the inside surface 152 and the insulating material of the outside surface 154 of the support envelope 122. As a result, positioning of the support envelope 122 in the manner shown in FIG. 18 prepares the knee area for the wrapping of the leg with the sterilized gauze roll material 54 and the ace bandage in the manner described hereinabove.

While the basic positioning of the strap 190 on the envelope 122 will allow the elongated envelope portion 158 to be positioned at the lateral side 40 and the elongated envelope portion 160 at the medial side 42, positive retention on the leg 30 can be provided by the additional straps 196, 198 above and below the knee area to allow flexure of the knee without interfereing with or causing damage to the incision area. As mentioned above, the devices of U.S. Pat. Nos. 4,026,299 and 4,523,594 would interfere with flexure and could damage the incision area.

It should be noted that the preferred support envelope 122 is shown an installed in a knee area. However, the same configuration can be employed to provide the adjustable opening for installation on a facial area similar to that shown in FIGS. 14 and 15 by the inclusion of additional securing strap means. The preferred configuration of employing the adjustable strap 190 in the area of the extended portion 181 insures that the opening length OL will be sufficiently large for application on either the knee area or in a facial area.

The preferred fluid circulating blanket 120 has a blanket width BW of about 12 inches and a blanket length BL of about 12 inches. The envelope width EW and envelope length EL are only slightly larger than the blanket width BW and blanket length BL for insertion of the blanket 120 within the interior 150 of the envelope 122. Each of the elongated portions 128, 132 has a portion width PW of about 5 inches. Additionally, the access width AW is about 9.5 inches. With the overall U-shape of the preferred blanket 120 and envelope 122, the envelope opening 170 has an opening width OW of at least 0.5 inches and an opening length OL of at least 8 inches for alignment with the mid-line incision which is produced during many forms of knee surgery. While the adjustable strap 190 might be selectively positioned at any location along the outside surface 154 of the envelope 122, the preferred location on the extended portion 181 allows the opening length OL to be at least 8 inches and as great as 10.5 inches as the strap 190 is located at least 8 inches and up to 10.5 inches from the connecting portion 62 of the envelope 122. Again, it should be noted that while the opening width OW is at least 0.5 inches, the opening width OW may be enlarged to about 2 inches for example with the adjustable strap 190 for installation on a knee but could be adjusted to even a wider dimension if installed by the use of additional straps in the manner generally shown for application to the facial area in FIGS. 14 and 15.

It should be noted that the preferred dimensions provided for the support envelope 122 are not simply a matter of design choice when one recognizes the existence of the prior art configurations employed in the blanket 82 of FIG. 10 and in the device disclosed in U.S. Pat. No. 1,860,847. While these devices may appear to have a configuration similar to that of the present support envelope 122, as discussed above, they would clearly be inappropriate for use following surgery in the knee area or in the facial area and do not suggest the particular configuration of the present invention which can be so employed.

Similarly, while the preferred envelope 122 and enclosed blanket 120 are sterilized for use following some form of surgery, the specific configuration, including the relatively narrow and relatively long elongated opening and elongated envelope opening of the types described, are particularly attractive for use therapeutically. For example, while the elongated openings will not interfere with incision in the knee area, they also allow full flexure of the blanket and envelope when installed at the knee area or on an elbow or the like. While some flexure of the knee is significant following surgery, it should be clear that even more flexure could be expected during therapy. Accordingly, the elongated openings 140, 170 would be even more appropriate for use with repeated and extensive flexure of a knee or elbow area during therapy. Without the openings of the type described, the heating or cooling of the knee or elbow area is not efficient and the joint is restricted to prevent full flexure.

The use of the preferred support envelope 122, when properly sterilized, clearly facilitates positioning of the blanket 120 on the patient and tends to insure proper positioning throughout the post-operative period. The preferred support envelopes will, again, reduce the time that a patient is anesthetized and will eliminate any need for tape to be directly applied to the patient as sometimes occurred in the prior art method of directing the blankets to the desired area.

Clearly, various modifications and alterations to the preferred embodiments and the method described herein could be provided by those skilled in the art without departing from the scope of the invention as claimed. For example, as indicated hereinabove, some fluid circulating blankets include a plastic container for the entrapment of moisture therein. It should be recognized that the various support envelopes could be formed of a laminated material to include plastic or other material at the interior side thereof for the retention of moisture. The sterile cloth material or the sterile insulating material with a loop outer surface might be laminated to the plastic material and the edges sealed together rather than simply stitched together. In fact, in some embodiments stitching may be replaced by heat or R.F. sealing (radio frequency sealing) to join various parts of the envelope and/or blanket. Still further, some fluid circulating blankets presently employ insulating material which appears to be laminated to one side of the blanket. The preferred support envelopes including the blankets therein would eliminate the need for insulating material directly laminated to the blanket. This insulating material is again primarily for retaining the heat or cold in the desired area of the body. Finally the availability of non-abrasive hook material for tabs or strips and/or the availability of other forms of hook accepting loop material that provides insulation could also result in further modifications of the specific embodiments shown herein while still being within the scope of the invention as claimed.

What is claimed is:

1. An apparatus for use with a temperature controlled fluid circulating device, said apparatus for controlling a temperature of an area of a body, said apparatus comprising:
   a fluid circulating blanket;
   said fluid circulating blanket having a first side and a second side;
   said fluid circulating blanket having two parallel elongated blanket portions and a connecting blanket portion therebetween;
   said parallel elongated blanket portions having first ends and second ends with said connecting blanket portion being at said first ends to form an elongated opening between said parallel elongated blanket portions;
   said fluid circulating blanket having fluid connection hose means extending from an edge of said second end of each of said parallel elongated blanket portions;
   said fluid connection hose means including an extended end adapted to be connected to the fluid circulating device;
   a support envelope surrounding said fluid circulating blanket to enclose at least said first side and said second side within an interior of said support envelope;
   said support envelope including an inside surface adjacent said first side and an outside surface adjacent said second side;
   said support envelope having two parallel elongated envelope portions and a connecting envelope portion therebetween;
   said parallel elongated envelope portions having envelope first ends and envelope second ends with said connecting envelope portion being at said envelope first ends to form an elongated envelope opening between said parallel elongated envelope portions;
   said elongated envelope opening being in alignment with said elongated opening of said fluid circulating blanket;
   said inside surface and said outside surface being joined at least at an edge of said elongated envelope opening;
   means for securely positioning said support envelope, with said fluid circulating blanket therein, with said inside surface of said support envelope against the area of the body;
   said inside surface of said support envelope including cloth material; and
   said outside surface of said support envelope including insulation material.

2. The apparatus of claim 1, wherein said support envelope includes an access opening at said first ends of said parallel elongated envelope portions and said connecting envelope portion therebetween for insertion of said fluid circulating blanket within said interior of said support envelope.

3. The apparatus of claim 2, wherein said fluid circulating blanket includes a blanket width along said first ends of said parallel elongated blanket portions and said blanket connecting portion, said access opening includes an access width along said first ends of said parallel elongated envelope portions and said connecting envelope portion, and said access width is less than said blanket width for retention of said fluid circulating blanket within said interior of said support envelope.

4. The apparatus of claim 2, wherein said each of said parallel elongated envelope portions includes a hose opening at said second envelope ends for extension of said fluid connection hose means from said interior of said support envelope to dispose said extended end outwardly of said support envelope.

5. The apparatus of claim 4, wherein said means for securely positioning said support envelope includes adjustable strap means extending between said second ends of said parallel elongated envelope portions and said adjustable strap means is for establishing an opening width of said elongated envelope opening at said second ends of said parallel elongated envelope portions.

6. The apparatus of claim 5, wherein said outside surface of said support envelope and said adjustable strap means includes releasable connecting surfaces therebetween.

7. The apparatus of claim 6, wherein said outer surface of said each of said parallel elongated envelope portions at said second end thereof includes an extended portion which extends beyond said second end of said each of said parallel elongated portions of said fluid circulating blanket.

8. The apparatus of claim 7, wherein said extended portion of said outer surface of said each of said parallel elongated envelope portions includes means for supporting said fluid connection hose means extending from said edge of said second end of said each of said parallel elongated blanket portions.

9. The apparatus of claim 8, wherein said adjustable strap means is secured to said extended portion of said outside surface of said each of said parallel elongated envelope portions.

10. An apparatus for use with a temperature controlled fluid circulating device, said apparatus for controlling a temperature of a surgically sterile area of a body which surgically sterile area surrounds a surgical region of the body following surgery, said apparatus comprising:
    a sterile fluid circulating blanket;
    said fluid circulating blanket having a first side and a second side;

said fluid circulating blanket having two parallel elongated blanket portions and a connecting blanket portion therebetween;
said parallel elongated blanket portions having first ends and second ends with said connecting blanket portion being at said first ends to form an elongated opening between said parallel elongated blanket portions;
said fluid circulating blanket having fluid connection hose means extending from an edge of said second end of each of said parallel elongated blanket portions;
said fluid connection hose means including an extended end adapted to be connected to the fluid circulating device;
a sterile support envelope surrounding said fluid circulating blanket to enclose at least said first side and said second side within an interior of said support envelope;
said support envelope including an inside surface adjacent said first side and an outside surface adjacent said second side;
said support envelope having two parallel elongated envelope portions and a connecting envelope portion therebetween;
said parallel elongated envelope portions having envelope first ends and envelope second ends with said connecting envelope portion being at said envelope first ends to form an elongated envelope opening between said parallel elongated envelope portions;
said elongated envelope opening being in alignment with said elongated opening of said fluid circulating blanket;
said inside surface and said outside surface being joined at least at an edge of said elongated envelope opening;
means for securely positioning said support envelope, with said fluid circulating blanket therein, with said inside surface of said support envelope against the surgically sterile area of the body;
said means for securely positioning is for aligning said elongated opening and said elongated envelope opening with the surgical region when said inside surface is against the surgically sterile area;
said inside surface of said support envelope including cloth material; and
said outside surface of said support envelope including insulation material.

11. An apparatus for use with a temperature controlled fluid circulating device, said apparatus for controlling a temperature of a surgically sterile area of a body which surgically sterile area surrounds a surgical region of the body following surgery, the surgery including a mid-line incision of a knee, the mid-line incision defining the surgical region, the surgically sterile area of the body being at opposite first and second sides of the knee and the mid-line incision thereof, said apparatus comprising:
a sterile fluid circulating blanket;
said fluid circulating blanket having a first side and a second side;
said fluid circulating blanket having two parallel elongated blanket portions and a connecting blanket portion therebetween;
said parallel elongated blanket portions having first ends and second ends with said connecting blanket portion being at said first ends to form an elongated opening between said parallel elongated blanket portions;
said fluid circulating blanket having fluid connection hose means extending from an edge of said second end of each of said parallel elongated blanket portions;
said fluid connection hose means including an extended end adapted to be connected to the fluid circulating device;
a sterile support envelope surrounding said fluid circulating blanket to enclose at least said first side and said second side within an interior of said support envelope;
said support envelope including an inside surface adjacent said first side and an outside surface adjacent said second side;
said support envelope having two parallel elongated envelope portions and a connecting enveloper portion therebetween;
said parallel elongated envelope portions having envelope first ends and envelope second ends with said connecting envelope portion being at said envelope first end to form an elongated envelope opening between said parallel elongated envelope portions;
said elongated envelope opening being in alignment with said elongated opening of said fluid circulating blanket;
said inside surface and said outside surface being joined at least at an edge of said elongated envelope opening;
means for securely positioning said support envelope, with said fluid circulating blanket therein, with said inside surface of said support envelope against the surgically sterile area of the body;
said means for securely positioning is for aligning said elongated opening and said elongated envelope opening with the mid-line incision when said inside surface is against the opposite first and second sides of the knee;
said elongated opening and said elongated envelope opening including an opening width of at least ½ inch and an opening length of at least 8 inches for alignment with the mid line incision;
said inside surface of said support envelope including cloth material; and
said outside surface of said support envelope including insulation material.

12. The apparatus of claim 11, wherein said parallel elongated envelope portions respectively are capable of overlaying the first and second sides of the knee.

13. The apparatus of claim 12, wherein said means for securely positioning said support envelope includes retaining strap means which a re sized to extend around a leg and said retaining strap means is sterile.

14. The apparatus of claim 11, wherein said means for securely positioning said support envelope includes adjustable strap means extending between said second ends of said parallel elongated envelope portions and said adjustable strap means is sterile.

15. The apparatus of claim 14, wherein said adjustable strap means is disposed at least 8 inches from said connecting envelope portion.

16. The apparatus of claim 15, wherein said adjustable strap means is for establishing said opening width of said elongated envelope opening at said second end of said parallel elongated envelope portions.

17. The apparatus of claim 11, wherein said fluid circulating blanket includes a blanket width of about 12 inches and a blanket length of about 12 inches.

18. The apparatus of claim 17, wherein said each of said parallel elongated blanket portions includes said blanket length of about 12 inches and a blanket portion width of at least 5 inches.

* * * * *